United States Patent [19]

Beck et al.

[11] Patent Number: 4,851,440

[45] Date of Patent: Jul. 25, 1989

[54] LEUKOTRIENE ANTAGONISTS, PROCESSES FOR THE PREPARATION THEREOF, THE USE THEREOF FOR THE TREATMENT OF DISEASES, AND PRECURSORS

[75] Inventors: Gerhard Beck; Peter Below; Andreas Bergmann, all of Frankfurt am Main, Fed. Rep. of Germany

[73] Assignee: Hoechst Aktiengesellschaft, Frankfurt am Main, Fed. Rep. of Germany

[21] Appl. No.: 222,975

[22] Filed: Jul. 22, 1988

[30] Foreign Application Priority Data

Jul. 25, 1987 [DE] Fed. Rep. of Germany ....... 3724735

[51] Int. Cl.[4] ................. A61K 31/215; C07C 149/273
[52] U.S. Cl. .................................... 514/550; 514/532; 514/570; 514/571; 514/618; 560/11; 560/15; 560/17; 560/60; 562/426; 562/429; 562/470; 564/161; 564/162; 564/169; 564/170
[58] Field of Search ...................... 560/15, 11, 60, 17; 562/426, 429, 470; 514/532, 570, 550, 571; 564/161, 162, 169, 170

[56] References Cited

U.S. PATENT DOCUMENTS

| | | | |
|---|---|---|---|
| 3,867,434 | 2/1975 | Diamond | 562/426 |
| 3,894,080 | 7/1975 | Diamond et al. | 564/162 |
| 3,993,683 | 11/1976 | Nickl et al. | 564/162 |
| 4,785,004 | 11/1988 | Von Sprecher et al. | 514/532 |

FOREIGN PATENT DOCUMENTS 2101594  1/1983  United Kingdom ................. 560/17

OTHER PUBLICATIONS

Musser et al., Agents and Actions, vol. 18, pp. 332–341 (1986).
Gleason et al., Journal of Medicinal Chemistry, vol. 30, No. 6, pp. 959–961 (1987).

Primary Examiner—James H. Reamer
Assistant Examiner—Julie K. Parker
Attorney, Agent, or Firm—Finnegan, Henderson, Farabow, Garrett, & Dunner

[57] ABSTRACT

Leukotriene antagonists, processes for the preparation thereof, the use thereof for the treatment of diseases, and precursors.

Compounds of the formula I

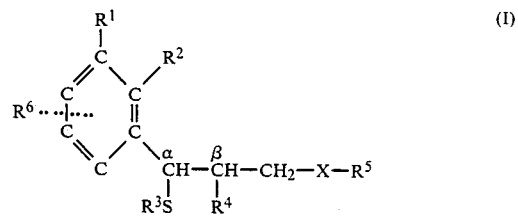

in which $R^1$, $R^2$, $R^3$, $R^4$, $R^5$, $R^6$ and X have the indicated meanings, processes for the preparation of these compounds, the use thereof as pharmaceuticals, and pharmaceutical products based on these compounds are described. In addition, precursors for the preparation of compounds of the formula I are described.

23 Claims, No Drawings

LEUKOTRIENE ANTAGONISTS, PROCESSES FOR THE PREPARATION THEREOF, THE USE THEREOF FOR THE TREATMENT OF DISEASES, AND PRECURSORS

DESCRIPTION

The invention relates to new chemical compounds which, as such or in the form of their pharmacologically tolerated salts, have a leukotriene-antagonistic action, to processes for the preparation of these compounds, to pharmaceutical agents which contain the active compounds according to the invention, and to the use thereof, especially for the treatment of diseases which are associated with an elevated leukotriene level, for example asthma.

In response to various stimuli, for example those elicited by allergens, basophilic cells and mast cells release a mediator which is called SRS-A (slow reacting substance of anaphylaxis) and which shows both in animal experiments and in humans an extremely strong bronchoconstricting effect and presumably plays an important part in asthmatic disorders. It was shown some years ago that SRS-A is a mixture of the peptido leukotrienes $LTC_4$, $LTD_4$ and $LTE_4$, which are produced from arachidonic acid via what is called the 5-lipoxygenase pathway. It is assumed that the leukotrienes also play an important part in other allergic and inflammatory disorders, such as allergic skin reactions, psoriasis, ulcerative colitis and rheumatoid arthritis, as well as in shock.

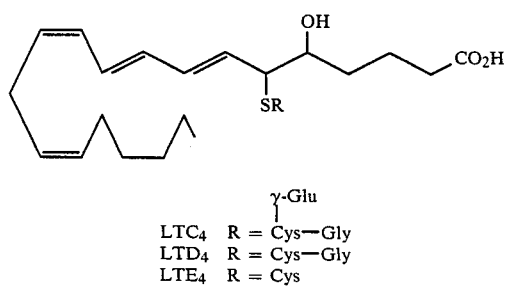

$LTC_4$  R = Cys—Gly
        |
        γ-Glu $LTD_4$  R = Cys—Gly $LTE_4$  R = Cys

The biological effect of the leukotrienes is mediated by specific receptors on the target cells (smooth muscle cells, macrophages etc.). This is why compounds which are able to block these receptors (i.e. receptor antagonists) ought to be suitable for the treatment of the abovementioned diseases.

It has already been described how certain alterations in the basic structure of the leukotrienes (saturation of some of the double bonds, incorporation of a benzene ring into the chain, shortening, modification or complete omission of the peptide side-chain or of the terminal carboxyl group) may result in partial agonists or antagonists (for a review, see John H. Musser et al., Agents and Actions 18, 332–41 (1986), and John G. Gleason et al., J. Med. Chem. 30 (6), 959–61, (1987)). However, many of the leukotriene analogs described hitherto still have agonistic properties or, apart from a few exceptions, have insufficient in vivo activity or no oral activity.

We have now found, surprisingly, that the basic structure of the leukotrienes can be even more extensively modified than hitherto described without losing the desired antagonistic action.

Hence the invention relates to new compounds of the general formula I:

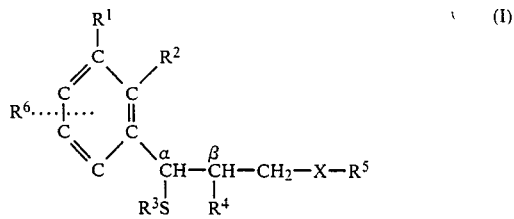

in which the radicals have the following meaning:

X is O, S, SO or $SO_2$;

$R^1$ is H, $C_1$–$C_{12}$-alkyl, $C_3$–$C_{12}$-alkenyl or $C_3$–$C_{12}$-alkynyl, $C_3$–$C_8$-cycloalkyl or $C_3$–$C_8$-cycloalkenyl, phenyl, halogen, $CF_3$, $NO_2$, phenoxy, OH, $OR^7$, COOH, $COOR^7$, CHO or $COR^8$;

$R^2$ is H, $C_1$–$C_{12}$-alkyl, $C_3$–$C_{12}$-alkenyl or $C_3$–$C_{12}$-alkynyl, phenyl-$C_1$–$C_{10}$-alkyl or a group OZ where Z is H, $C_1$–$C_{12}$-alkyl, $C_3$–$C_{12}$-alkenyl or $C_3$–$C_{12}$-alkynyl, $C_3$–$C_8$-cycloalkyl or $C_3$–$C_8$-cycloalkenyl, phenyl, phenyl-$C_1$–$C_{10}$-alkyl, phenyl-$C_3$–$C_{10}$-alkenyl, phenyl-$C_3$–$C_{10}$-alkynyl or phenoxy-$C_2$–$C_6$-alkyl, it also being possible for the phenyl rings to be substituted by 1–3 $C_1$–$C_4$-alkyl, $C_2$–$C_4$-alkenyl, $C_1$–$C_4$-alkoxy, $C_1$–$C_4$-alkanoyl, $C_1$–$C_4$-alkoxycarbonyl, hydroxyl or halogen radicals, or Z is pyridylmethyl or thienylmethyl;

$R^3$ is phenyl which is optionally substituted with 1–3 amino, halogen, hydroxyl, $C_1$–$C_4$-alkoxy, $C_1$–$C_4$-alkyl or $C_1$–$C_4$-alkylthio radicals, or $R^3$ is naphthyl, $(CH_2)_mCO_2H$ or $(CH_2)_mCO_2$—$C_1$–$C_4$-alkyl;

$R^4$ is OH, $C_1$–$C_4$-alkoxy or $OCOR^8$;

$R^5$ is $C_1$–$C_4$-alkyl, $C_2$–$C_4$-hydroxyalkyl, $C_1$–$C_4$-alkoxy-$C_1$–$C_4$-alkyl, $C_1$–$C_4$-alkanoyloxy-$C_1$–$C_4$-alkyl, phenyl or phenyl-$C_1$–$C_4$-alkyl, it being possible for the phenyl rings to be substituted once or twice with HO, halogen, $C_1$–$C_4$-alkoxy, $C_1$–$C_4$-alkoxycarbonyl or $C_1$–$C_4$-alkylthio, or $R^5$ is a group of the general formula $(CH_2)_nCOR^9$ or $(CH_2)_nR^{10}$ or of the formula II;

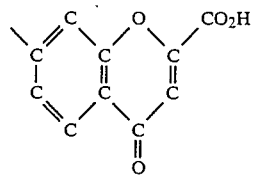

$R^6$ is H, halogen, $CF_3$, OH, $C_1$–$C_4$-alkyl, or $C_1$–$C_4$-alkoxy;

$R^7$ is $C_1$–$C_4$-alkyl, allyl or benzyl;

$R^8$ is $C_1$–$C_4$-alkyl;

$R^9$ is OH, $C_1$–$C_7$-alkoxy, $OCH_2Ph$, NHOH, $NH_2$, $NHR^8$, $NR^8_2$, piperidino, pyrrolidino, morpholino, or 2-carboxyphenoxy $R^{10}$ is tetrazol-5-yl;

m is 1, 2, 3 or 4;

n is 0, 1, 2 or 3;

as well as to physiologically tolerated salts of those compounds of the general formula I in which one of the radicals contains a carboxyl group (COOH).

Preferred compounds of the general formula I are those in which the radicals have the following meaning:

X is O, S, SO or $SO_2$;

$R^1$ is H, $C_3$–$C_8$-cycloalkyl or $C_3$–$C_8$-cycloalkenyl;

R² is H, $C_8$-$C_{12}$-alkyl or $C_3$-$C_{12}$-alkenyl (straight-chain), phenyl-$C_1$-$C_{10}$-alkyl, or a group OZ, where Z is $C_1$-$C_{12}$-alkyl, $C_3$-$C_8$-cycloalkyl, phenyl, phenyl-$C_1$-$C_{10}$-alkyl or phenoxy-$C_2$-$C_6$-alkyl, it also being possible for the phenyl rings to be substituted by one to three methoxycarbonyl, acetyl, hydroxyl, $C_1$-$C_4$-alkyl or methoxy groups, or Z is pyridylmethyl or thienylmethyl;

R³ is phenyl which is optionally substituted with one to three amino, halogen, hydroxyl, $C_1$-$C_4$-alkoxy, $C_1$-$C_4$-alkyl or $C_1$-$C_4$-alkylthio radicals, or R³ is naphthyl, $(CH_2)_mCO_2H$ or $(CH_2)_mCO_2$—$C_1$-$C_4$-alkyl;

R⁴ is OH;

R⁵ is $C_1$-$C_4$-alkyl, hydroxy-$C_2$-$C_4$-alkyl, $C_1$-$C_4$-alkoxy-$C_1$-$C_4$-alkyl, $C_1$-$C_4$-alkanoyloxy-$C_1$-$C_4$-alkyl, phenyl or phenyl-$C_1$-$C_4$-alkyl, it being possible for the phenyl rings to be substituted once or twice with HO, halogen, $C_1$-$C_4$-alkoxy, $C_1$-$C_4$-alkoxycarbonyl or $C_1$-$C_4$-alkylthio, or is a group of the general formula $(CH_2)_nCOR^9$ or $(CH_2)_nR^{10}$ or of the formula II;

R⁶ is H, halogen, $C_1$-$C_4$-alkyl or $C_1$-$C_4$-alkoxy;

R⁸ is $C_1$-$C_4$-alkyl;

R⁹ is OH, $C_1$-$C_7$-alkoxy, $NH_2$, NHOH;

R¹⁰ is tetrazol-5-yl;

m is 1, 2, 3 or 4;

n is 1, 2 or 3.

Particularly preferred compounds of the general formula I are those in which the radicals have the following meaning:

X is O or S;

R¹ is H or cyclopentyl

R² is H, $C_8$-$C_{12}$-alkyl or $C_3$-$C_{12}$-alkenyl (straight-chain), phenyl-$C_6$-$C_{10}$-alkyl, or a group OZ, where Z is $C_1$-$C_{12}$-alkyl or phenyl-$C_1$-$C_{10}$-alkyl, it also being possible for the phenyl rings to be substituted by methoxycarbonyl or methoxy, or Z is pyridylmethyl or thienylmethyl;

R³ is phenyl which is optionally substituted with an amino, hydroxyl, methoxy, methyl or methylthio radical, or R³ is naphthyl, $(CH_2)_mCO_2H$ or $(CH_2)_mCO_2$-$C_1$-$C_4$-alkyl;

R⁴ is OH;

R⁵ is $C_1$-$C_4$-alkyl, hydroxy-$C_2$-$C_4$-alkyl, $C_1$-$C_4$-alkoxy-$C_1$-$C_4$-alkyl, $C_1$-$C_4$-alkanoyloxy-$C_1$-$C_4$-alkyl or a group of the general formula $(CH_2)_nCOR^9$;

R⁶ is H, halogen, $C_1$-$C_4$-alkyl or $C_1$-$C_4$-alkoxy;

R⁹ is OH, $C_1$-$C_7$-alkoxy, $NH_2$, NHOH;

m is 1, 2, 3 or 4;

n is 1, 2 or 3.

The invention particularly preferably relates to the following compounds:

Methyl (5RS,6SR)-5-hydroxy-6-(3-methoxyphenylthio)-6-phenyl-3-oxahexanoate

Dimethyl (5RS,6SR)-5-hydroxy-6-phenyl-3-oxa-7-thianonanedioate

Dimethyl (5RS,6SR)-5-hydroxy-6-phenyl-3-oxa-7-thiadecanedioate

Methyl (5RS,6SR)-5-hydroxy-6-(3-methoxyphenylthio)-6-phenyl-3-thiahexanoate

Methyl (5S,6R)-(−)-5-hydroxy-6-(3-methoxyphenylthio)-6-phenyl-3-thiahexanoate

Methyl (5R,6S)-(+)-5-hydroxy-6-(3-methoxyphenylthio)-6-phenyl-3-thiahexanoate

Dimethyl (5RS,6RS)-5-hydroxy-6-phenyl-3,7-dithiadecanedioate

Methyl (5RS,6SR)-5-hydroxy-6-(3-methoxyphenylthio)-6-(2-benzyloxy-3-cyclopentylphenyl)-3-oxahexanoate Dimethyl (5RS,6SR)-5-hydroxy-6-(2-benzyloxy-3-cyclopentylphenyl)-3-oxa-7-thianonanedioate Dimethyl (5RS,6SR)-5-hydroxy-6-(2-benzyloxy-3-cyclopentylphenyl)-3-oxa-7-thiadecanedioate Methyl (5RS,6SR)-5-hydroxy-6-(3-methoxyphenylthio)-6-(2-benzyloxy-3-cyclopentylphenyl)-3-thiahexanoate Dimethyl (5RS,6RS)-5-hydroxy-6-(2-benzyloxy-3-cyclopentylphenyl)-3,7-dithiadecanedioate Dimethyl (5RS,6RS)-5-hydroxy-6-[2-(4-methoxybenzyloxy)-3-cyclopentylphenyl]-3,7-dithiadecanedioate Methyl (5RS,6SR)-5-hydroxy-6-(3-methoxyphenylthio)-6-[2-(4-methoxybenzyloxy)-3-cyclopentylphenyl]-3-thiahexanoate (5S,6R)-(−)-5-Hydroxy-6-(3-methoxyphenylthio)-6-phenyl-3-thiahexanoic acid.

As is evident from the general formula I, the compounds according to the invention contain two asymmetric carbon atoms (those on which the radicals R³S and R⁴ are located). They can therefore occur in the form of two diastereomers, each of which is in turn composed of two enantiomers. Hence the invention also relates to the pure diastereomers and enantiomers of the compounds according to the invention. The diastereomers with the relative configuration (RS) at C-α and (SR) at C-β, and the corresponding enantiomers, are preferred.

The invention furthermore relates to the new epoxides of the general formula III

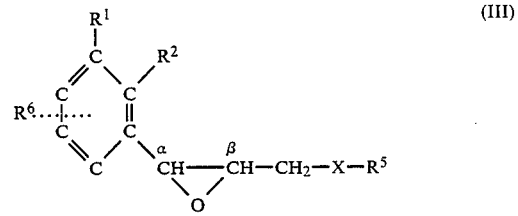

where the radicals R¹, R², R⁵, R⁶ and X have the same meaning as in formula I. These compounds are valuable intermediates for the synthesis of the compounds of the general formula I according to the invention. The compounds of the general formula III can exist as cis- or trans-diastereomers, and each of the diastereomers can in turn exist as the dextrorotatory or levorotatory enantiomer. Hence the invention relates both to the pure diastereomers as racemate and to the pure enantiomers. The trans-diastereomers of the general formula IIIa (see scheme 1) are preferred.

The invention furthermore relates to processes for the preparation of the compounds of the formula I according to the invention.

The processes comprise (A) a compound of the general formula III in which R¹, R², R⁵, R⁶ and X have the meanings mentioned for formula I being reacted with a thiol of the general formula R³SH, where R³ has the meaning mentioned for formula I, to give a compound of the formula I in which R¹, R², R³, R⁵, R⁶ and X have the indicated meaning, and R⁴ is the hydroxyl group, or (B) a compound of the general formula IV

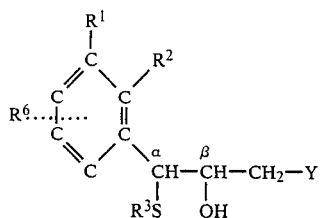

with a thiol of the general formula $R^5SM$, where $R^5$ has the meaning mentioned for formula I, and M denotes hydrogen or an alkali metal, to give a compound of the formula I in which $R^1$, $R^2$, $R^3$, $R^5$ and $R^6$ have the indicated meaning, $R^4$ denotes the hydroxyl group and X denotes sulfur, and, where appropriate, a resulting compound being converted by modification into another compound of the formula I.

Scheme 1

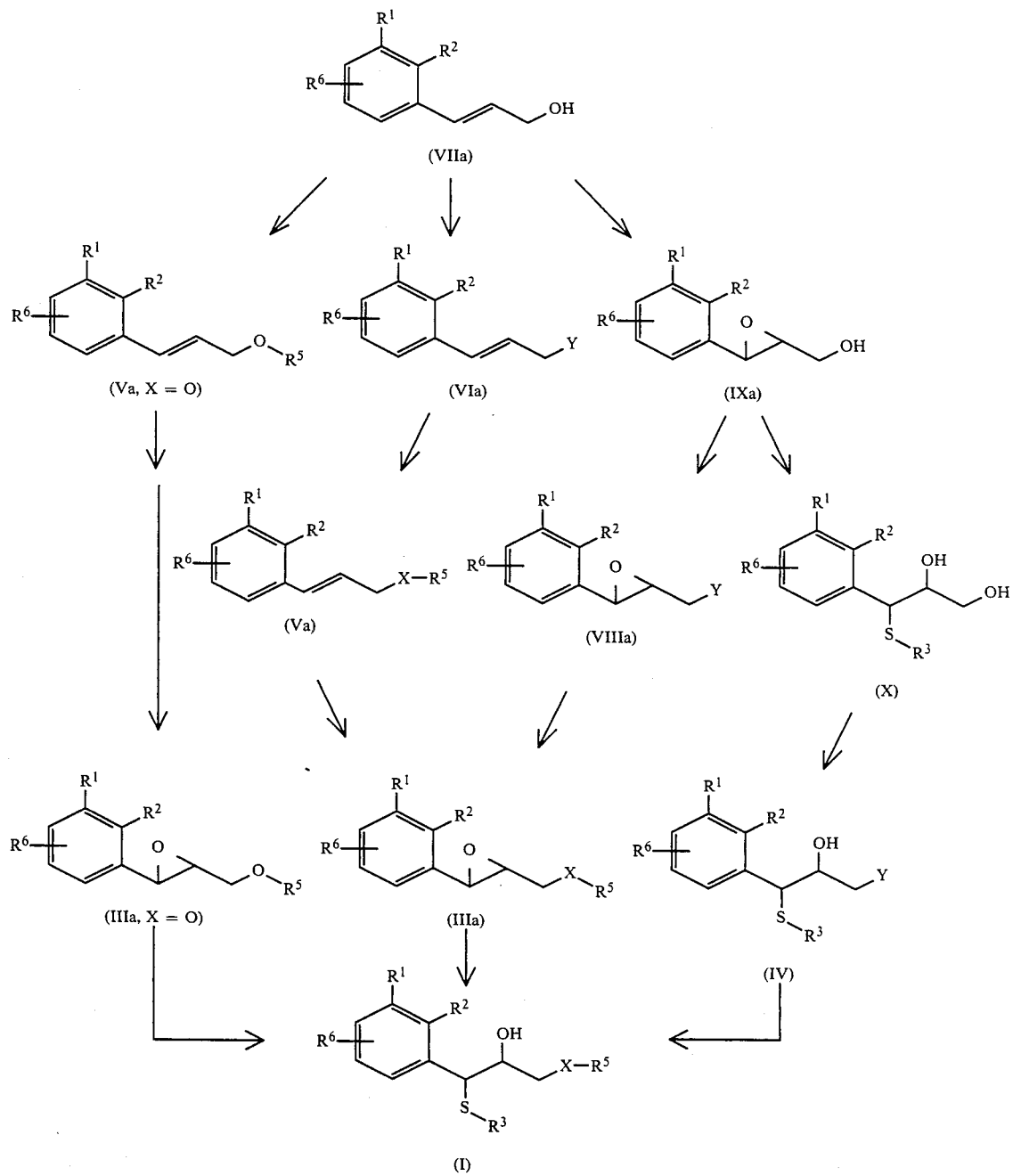

in which $R^1$, $R^2$, $R^5$, $R^6$ and X have the meanings mentioned for formula I, and Y is a leaving group, such as methanesulfonyloxy, trifluoromethanesulfonyloxy, benzenesulfonyloxy or p-toluenesulfonyloxy, being reacted Preferred processes are those in which a specific one of the possible diastereomers or enantiomers is produced. Scheme 1 summarizes the most important synthetic routes taking the example of the transdiastereomer.

The compounds of the general formula I, according to the invention, in which $R^4$ is OH can be obtained as described above by process A by reaction of compounds of the general formula III with mercaptans $R^3SH$.

The reaction is advantageously carried out in an organic solvent such as toluene, tetrahydrofuran, diethyl ether, tert.butyl methyl ether, dimethylformamide, dimethyl sulfoxide or a lower alcohol such as methanol, ethanol, isopropanol or tert.butanol in the presence of a base. Bases which can be used are alkali metal and alkaline earth metal carbonates and hydroxides, or amines, especially tert.amines, particularly trialkylamines, preferably triethylamine, diisopropylethylamine or 1,4-diazabicyclo[2.2.2]octane (DABCO), or tertiary amidines, particularly bicyclic amidines, preferably 1,5-diazabicyclo[4.3.0]non-5-ene (DBN) or 1,8-diazabicyclo[5.4.0]undec-7-ene (DBU). When the reaction with the mercaptans $R^3SH$ is carried out in a lower alcohol, it is also possible, advantageously, for the corresponding sodium or potassium alcoholates to be used as base; in this case catalytic quantities of the alcoholate (1–20 mol-%) often suffice.

The reaction is carried out at temperatures from $-20°$ C. to the boiling point of the solvent used. A temperature range from $0°$ to $120°$ C. is preferred, particularly from $20°$ to $80°$ C.

The preferred embodiment of process A for the preparation of compounds of the formula I, according to the invention, in which $R^4$ is OH comprises reacting a compound of the formula III with a mercaptan $R^3SH$ in the presence of triethylamine and/or DBU in tetrahydrofuran or methanol (if one of the R groups contains an ester, it is advantageous to use the alcohol contained in this ester) at temperatures of from $20°$ to $60°$ C. It is also advantageous for the reaction to be carried out under a protective gas (nitrogen or argon).

The relative and absolute configuration of the compounds of the general formula I obtained by process A depends on the relative and absolute configuration of the compound of the general formula III used. When the racemic trans-epoxide (general formula IIIa) is used, the product I is obtained in the relative configuration $\alpha(RS)$, $\beta(SR)$; when an optically active trans-epoxide (for example $\alpha(S)$) is used, the product I obtained analogously is the $\alpha(R)$, $\beta(S)$-enantiomer. The other possible stereoisomers of the product I are obtained analogously from the corresponding stereoisomers of III.

The compounds of the general formula I, according to the invention, in which $R^4$ is OH and X is S can also be obtained by process B by reaction of a compound of the general formula IV with mercaptans $R^5SH$ or the alkali metal salts thereof.

The reaction is advantageously carried out in an organic solvent such as toluene, tetrahydrofuran, diethyl ether, tert.butyl methyl ether, dimethylformamide, dimethyl sulfoxide or a lower alcohol such as methanol, ethanol, isopropanol or tert.butanol in the presence of a base. Suitable bases are alkali metal carbonates, hydroxides, alcoholates or hydrides; the preferred base is sodium hydride.

A particularly favorable variant of process B comprises reacting a compound of the general formula IV with a compound of the general formula $R^5SM$ in which $R^5$ has the same meaning as in formula I, and M is an alkali metal, especially sodium, in an inert solvent such as tetrahydrofuran, dimethylformamide or dimethyl sulfoxide. The required compounds $R^5SM$ can easily be prepared in a separate step from the corresponding mercaptan $R^5SH$ and and alkali metal hydride MH (especially sodium hydride) in an aprotic solvent such as n-hexane, cyclohexane, toluene or diethyl ether.

The reaction is carried out in a temperature range from $-20°$ C. to the boiling point of the solvent used, preferably in a range of $0°-80°$ C., especially of $0°-50°$ C.

A number of compounds of the general formula I according to the invention can be obtained by modifying other compounds of the formula I according to the invention.

Compounds of the general formula I in which $R^4$ is $OR^7$ can be obtained by process C. Process C comprises a compound of the general formula I in which $R^4$ is OH being reacted with a compound of the general formula $R^7Y$, where $R^7$ has the meaning mentioned for formula I, and Y is a leaving group such as Cl, Br, I or $OSO_2W$ ($W=CH_3$, Ph, tolyl, $CF_3$ or $OR^7$). The reaction is advantageously carried out in an inert organic solvent such as toluene, tetrahydrofuran, diethyl ether, tert.butyl methyl ether, dimethylformamide or dimethyl sulfoxide in the presence of a base. Suitable bases are particularly strong bases such as potassium tert.butylate, sodium hydride or lithium alkyls (preferably n-butyllithium); sodium hydride is preferred.

The reaction is carried out at temperatures from $-20°$ C. to the boiling point of the solvent used. A temperature range from $0°$ to $120°$ C. is preferred, particularly from $20°$ to $80°$ C.

The preferred embodiment of process C for the preparation of compounds of the formula I, according to the invention, in which $R^4$ is $OR^7$ comprises reacting a compound of the general formula I in which $R^4$ is OH with a compound $R^7Y$ in the presence of sodium hydride in dimethylformamide or tetrahydrofuran at temperatures from $20°$ to $60°$ C. It is advantageous for this reaction to be carried out with exclusion of moisture or under a protective gas (nitrogen or argon).

Compounds of the general formula I in which $R^4$ is $OCOR^8$ can be prepared by process D. Process D comprises a compound of the general formula I in which $R^4$ is OH being acylated with a compound of the general formula $R^8COCl$, $R^8COBr$ or $(R^8CO)_2O$, where $R^8$ has the meaning mentioned for formula I. The reaction is advantageously carried out in pyridine or in a mixture of pyridine with an inert organic solvent such as toluene, tetrahydrofuran, diethyl ether, methylene chloride or tert.butyl methyl ether. The reaction rate can be increased by addition of 5–100 mol-% of an acylation catalyst such as 4-dimethylaminopyridine, 4-pyrrolidinopyridine or 4-piperidinopyridine.

The reaction is carried out at temperatures from $-20°$ C. to the boiling point of the solvent used. A temperature range from $-20°$ to $50°$ C. is preferred, particularly from $0°$ to $25°$ C.

The preferred embodiment process D for the preparation of compounds of the formula I, according to the invention, in which $R^4$ is $OCOR^8$ comprises reacting a compound of the general formula I in which $R^4$ is OH with an organic acid chloride $R^8COCl$ or anhydride $(R^8CO)_2O$ in pyridine in the presence of 10–20 mol-% of 4-dimethylaminopyridine at temperatures from $0°$ to $20°$ C. It is advantageous for this reaction to be carried out with exclusion of moisture or under a protective gas (nitrogen or argon).

Compounds of the general formula I in which $R^4$ is $OCOR^8$ can also be prepared by process E. Process E comprises a compound of the general formula I in which $R^4$ is OH initially being converted into an activated derivative of the general formula XI

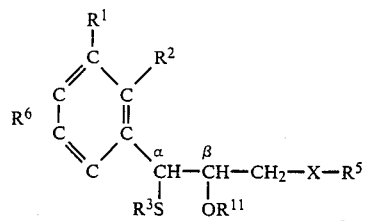
(XI)

in which the radicals $R^1$, $R^2$, $R^3$, $R^5$, $R^6$ and X have the meaning indicated for formula I, and $R^{11}$ is $CH_3SO_2$, $CF_3SO_2$, phenylsulfonyl or tolylsulfonyl, and this derivative then being reacted with a salt (sodium, potassium, cesium, trialkylammonium or tetraalkylammonium salt) or a carboxylic acid of the general formula $R^8COOH$, where $R^8$ has the meaning mentioned for the formula I. The derivative XI is prepared by standard methods known to the expert, by reaction of I ($R^4$=OH) with a sulfonyl chloride $R^{11}Cl$. This reaction is advantageously carried out in pyridine or in a mixture of pyridine or triethylamine with an inert organic solvent such as toluene, tetrahydrofuran, diethyl ether, methylene chloride or tert.butyl methyl ether at temperatures from $-40°$ to $+50°$ C., preferably at $-15°$ to $+15°$ C., with exclusion of moisture.

The reaction of the derivative XI with the salt of the carboxylic acid $R^8COOH$ is preferably carried out in a polar aprotic organic solvent such as acetone, butanone, dimethylformamide, N,N-dimethylacetamide, N-methylpyrrolidone or dimethyl sulfoxide; it is also possible in the case of the tri- or tetraalkylammonium salts for a non-polar aprotic solvent such as toluene, xylene, cyclohexane or petroleum ether to be used. The reaction is carried out at temperatures from 20° C. to the boiling point of the solvent used, preferably in a range from 20° to 120° C., especially from 20° to 80° C.

A particularly favorable embodiment of process E is the reaction of a compound of the general formula I in which $R^4$ is OH with a carboxylic acid $R^8COOH$ in the presence of an azodicarboxylic ester, for example a diethyl azodicarboxylate, and of a trialkyl- or triarylphosphine, for example tributylphosphine or triphenylphosphine, the so-called Mitsunobu reaction. In this case the derivatization and substitution take place in one step. The reaction is carried out in an aprotic organic solvent, preferably an ether such as tetrahydrofuran, 1,2-dimethoxyethane, dioxane, tert.butyl methyl ether or diethylene glycol dimethyl ether, at temperatures of from 0° C. to the boiling point of the solvent used, preferably 20° to 100° C., especially 20° to 60° C., under a protective gas ($N_2$, argon).

A particular feature of process E is the inversion of configuration at carbon atom $\beta$ of the general formula I which takes place during the reaction. Hence this process is suitable for preparing from the diastereomers of the $\alpha(RS)$, $\beta(SR)$ series those of the $\alpha(RS)$, $\beta(RS)$ series, and vice versa.

The compounds of the general formula I, according to the invention, in which $R^4$ is OH can also be obtained by process F. Process F comprises a compound of the general formula I in which $R^4$ is $OCOR^8$ being subjected to hydrolysis, aminolysis (each is applicable only if none of the other radicals contains an ester) or transesterification. The preferred process is transesterification, which is carried out in a lower alcohol, especially methanol or ethanol, in the presence of a basic catalyst such as sodium carbonate, potassium carbonate or the lithium, sodium or potassium alcoholate of the alcohol used. The preferred base is potassium carbonate. The reaction temperature is between 0° C. and the boiling point of the alcohol used, preferably between 0° and 80° C., especially between 20° and 50° C.

Compounds of the general formula I in which $R^5$ is $C_1$–$C_4$-alkanoyloxy-$C_2$–$C_4$-alkyl can also be prepared by process G. Process G comprises a compound of the general formula I in which $R^5$ is $C_2$–$C_4$-hydroxyalkyl being acylated with a $C_1$–$C_4$-carboxylic acid chloride or anhydride. In principle, the reaction is carried out in a manner known per se, advantageously in pyridine or in a mixture of pyridine with an inert organic solvent such as toluene, tetrahydrofuran, diethyl ether, methylene chloride or tert.butyl methyl ether. The reaction rate can be increased by addition of 5-100 mol-% of an acylation catalyst such as 4-dimethylaminopyridine, 4-pyrrolidinopyridine or 4-piperidinopyridine.

The reaction is carried out at temperatures from $-20°$ C. to the boiling point of the solvent used. A temperature range from $-20°$ to 50° C. is preferred, especially from 0° to 25° C.

Compounds of the general formula I in which $R^5$ is $C_1$–$C_4$-alkoxy-$C_2$–$C_4$-alkyl can also be prepared by process H. Process H comprises a compound of the general formula I in which $R^5$ is $C_2$–$C_4$-hydroxyalkyl being alkylated with a $C_1$–$C_4$-alkyl halide, sulfonate or sulfate. The reaction is advantageously carried out in an inert organic solvent such as tetrahydrofuran, diethyl ether, tert.butyl methyl ether, toluene, dimethylformamide or dimethyl sulfoxide, in the presence of a base. Suitable bases are particularly strong bases such as potassium tert.butylate, sodium hydride or lithium alkyls (preferably n-butyllithium); sodium hydride is preferred.

The reaction is carried out at temperatures from $-20°$ C. to the boiling point of the solvent used. A temperature range from 0° to 120° C. is preferred, especially from 20° to 80° C.

Compounds of the general formula I in which $R^5$ is $(CH_2)_nCOOH$, and n is 1-3, can also be prepared by process I. Process I comprises a compound of the general formula I in which $R^5$ is $C_2$–$C_4$-hydroxyalkyl being reacted with suitable oxidizing agents which are known in principle to the expert. The choice of the oxidizing agent is determined by the nature of the other radicals in the molecule. Suitable examples are pyridinium dichromate in dimethylformamide, chromic/sulfuric acid in water, acetic acid or acetone (Jones oxidation) or ruthenium trichloride (catalytic quantities) in the presence of cooxidants such as $K_2S_2O_8$ or $NaIO_4$ in water/$CCl_4$-acetonitrile or water/$CH_2Cl_2$ systems.

The reaction is carried out at temperatures from $-20°$ C. to the boiling point of the solvent used. A temperature range from 0° to 50° C. is preferred, especially from 0° to 30° C.

Compounds of the general formula I in which $R^5$ is $C_2$–$C_4$-hydroxyalkyl can also be prepared by process J. Process J comprises a compound of the general formula I in which $R^5$ is $(CH_2)_nCOR^9$, n is 1-3 and $R^9$ is OH or $C_1$–$C_7$-alkoxy being reacted with suitable reducing agents which are known to the expert. Particularly suitable are complex hydrides such as borane (preferably as complex with dimethyl sulfide or tetrahydrofuran), sodium borohydride, lithium borohydride, lithium aluminum hydride, diisobutylaluminum hydride and aluminum hydride. The reaction is advantageously carried out in an inert organic solvent such as toluene, tetrahydrofuran, diethyl ether, tert.butyl methyl ether or methylene chloride.

The reaction is carried out at temperatures from −20° C. to the boiling point of the solvent used. A temperature range from 0° to 100° C. is preferred, especially from 0° to 60° C.

Compounds of the general formula I in which $R^5$ is $C_2$–$C_4$-hydroxyalkyl can also be prepared by process K. Process K comprises a compound of the general formula I in which $R^5$ is $C_1$–$C_4$-alkanoyloxy-$C_2$–$C_4$-alkyl being cleaved by hydrolysis, aminolysis (each is applicable only if none of the other radicals contains an ester) or transesterification.

The hydrolysis is carried out in the presence of a base such as sodium hydroxide, potassium hydroxide, barium-hydroxide, calcium hydroxide, potassium carbonate, sodium carbonate or a sodium or potassium alcoholate; the aminolysis is carried out in the presence of an amine such as ammonia, $C_1$–$C_4$-alkylamines, ethylenediamine or 2-aminoethanol. The solvents used are lower alcohols or alcohol/water mixtures; it is also possible in the case of the amines to operate without a solvent.

The preferred form of this process is transesterification, which is carried out in a lower alcohol, especially methanol or ethanol, in the presence of a basic catalyst such as sodium carbonate, potassium carbonate or the lithium, sodium or potassium alcoholate of the alcohol used. The preferred base is potassium carbonate. The reaction temperature is between 0° C. and the boiling point of the alcohol used, preferably between 0° and 80° C., especially between 20° and 50° C.

Compounds of the general formula I in which $R^5$ is $(CH_2)_nCOR^9$, n is 1–3 and $R^9$ is OH can also be prepared by process L. Process L comprises a compound of the general formula I in which $R^5$ is $(CH_2)_nCOR^9$, n is 1–3 and $R^9$ is $C_1$–$C_7$-alkoxy being hydrolysed by standard processes known to the expert. Particularly suitable is alkaline hydrolysis with bases such as sodium hydroxide, potassium hydroxide, barium hydroxide, calcium hydroxide, sodium carbonate or potassium carbonate in a lower alcohol or alcohol/water mixtures.

The reaction is carried out at temperatures from 0° C. to the boiling point of the solvent used. A temperature range from 20° to 100° C. is preferred, especially from 20° to 70° C.

Compounds of the general formula I in which $R^5$ is $(CH_2)_nCOR^9$, n is 1–3 and $R^9$ is $C_1$–$C_7$-alkoxy can also be prepared by process M. Process M comprises a compound of the general formula I in which $R^5$ is $(CH_2)_nCOR^9$, n is 1–3 and $R^9$ is OH being esterified by standard processes known to the expert. Particularly suitable is alkylating esterification by reaction with a $C_1$–$C_7$-alkyl halide, sulfonate or sulfate in the presence of a base such as potassium carbonate, cesium carbonate, potassium fluoride, cesium fluoride, $C_1$–$C_4$-diazabicyclo[2.2.2]octane (DABCO), 1,5-diazabicyclo[4.3.0]non-5-ene (DBN) or 1,8-diazabicyclo[5.4.0]undec-7-ene (DBU) in a polar aprotic solvent such as acetone, butanone, acetonitrile, dimethylformamide, N,N-dimethylacetamide or N-methylpyrrolidone. Also suitable for the preparation of the methyl ester is reaction with diazomethane in diethyl ether, tetrahydrofuran or tert.butyl methyl ether.

The reaction is carried out at temperatures from 0° C. to the boiling point of the solvent used. A temperature range from 20° to 100° C. is preferred, especially from 20° to 50° C.

Compounds of the general formula I in which $R^5$ is $(CH_2)_nCOR^9$, n is 1–3 and $R^9$ is $C_1$–$C_7$-alkoxy can also be prepared by process N. Process N comprises another compound of the same formula being transesterified by standard processes known to the expert (replacement of the alkoxy radical by another alkoxy radical). It is preferable to use as solvent for this reaction the alcohol which corresponds to the alkoxy radical which is to be introduced; catalysts which can be used are either acids such as sulfuric acid, hydrochloric acid, p-toluenesulfonic acid, benzenesulfonic acid, methanesulfonic acid, camphorsulfonic acid or acid ion exchanger resins, or bases such as potassium carbonate, sodium carbonate, the lithium, sodium, potassium or titanium alcoholate corresponding to the alcohol used as solvent, or titanium tetraisopropylate. Basic catalysts are preferred in this case.

The reaction is carried out at temperatures from 0° C. to the boiling point of the solvent used. A temperature range from 20° to 100° C. is preferred, especially from 20° to 80° C.

Compounds of the general formula I in which $R^5$ is $(CH_2)_nCOR^9$, n is 1–3 and $R^9$ is NHOH, $NH_2$, $NHR^8$, $NR^8_2$ piperidino, pyrrolidino or morpholino can also be prepared by process O. Process O comprises a compound of the general formula I in which $R^5$ is $(CH_2)_nCOOH$ and n is 1–3 being condensed with the appropriate amine $R^9H$ by processes which are known in principle to the expert. A wide range of experience from peptide chemistry is available for this. Examples of suitable condensing agents are carbonyldiimidazole, dicyclohexylcarbodiimide, diethoxyphosphonyl chloride, diethoxyphosphonyl azide, phosphorus oxychloride, propylphosphonic anhydride and diphenylphosphonyl chloride.

The condensation is advantageously carried out in a solvent. Virtually all familiar organic solvents are suitable, depending on the condensing agent used, such as hydrocarbons (saturated or aromatic), chlorinated hydrocarbons, ethers, lower ketones such as acetone or butanone, tert.amides such as dimethylformamide, dimethylacetamide or N-methylpyrrolidone, lower alcohols such as methanol, ethanol, isopropanol, n-, iso- or tert.butanol and even aqueous systems or mixtures (homogeneous or two-phase) of water with the organic solvents listed.

A preferred embodiment of this process comprises reacting the compounds of the general formula I in which $R^5$ is $(CH_2)_nCOOH$ and n is 1–3 with carbonyldiimidazole in an aprotic solvent, especially tetrahydrofuran, at temperatures from 0° to 20° C., followed by addition of the amine component $R^9H$.

Alternatively, the carboxylic acid component can first be converted into an activated derivative (acid chloride, mixed anhydride) and the latter can then be reacted with the amine $R^9H$, preferably in the presence of an auxiliary base such as sodium bicarbonate, sodium carbonate, potassium carbonate, sodium hydroxide solution or potassium hydroxide solution, or a tertiary amine such as pyridine, lutidine or a trialkylamine such as triethylamine, diisopropylethylamine or tributylamine. The expert is familiar with a large number of methods for activating carboxylic acids, for example reaction with thionyl chloride, phosphorus trichloride, phosgene or oxalyl chloride to give the acid chloride, or reaction with chloroformic esters or sulfonyl chlorides, (methanesulfonyl chloride, trifluoromethanesulfonyl chloride or benzenesulfonyl chloride) in the presence of bases, preferably of tert.amines such as triethylamine or pyridine, to give the mixed anhydrides.

A preferred embodiment of this process comprises reacting the compounds of the general formula I in which $R^5$ is $(CH_2)_nCOOH$ and n is 1–3 with ethyl chloroformate in the presence of triethylamine in methylene chloride at temperatures from −20° to 5° C., followed by addition of the amine component $R^9H$.

Compounds of the general formula I in which $R^5$ is $(CH_2)_nCOR^9$, n is 1–3 and $R^9$ is NHOH, $NH_2$, $NHR^8$, $NR^8_2$, piperidino, pyrrolidino or morpholino can also be prepared by process P. Process P comprises reacting a compound of the general formula I in which $R^5$ is $(CH_2)_nCO$-$C_1$-$C_7$-alkoxy and n is 1–3 with the appropriate amine $R^9H$ (aminolysis). The reaction is preferably carried out in a suitable organic solvent such as an alcohol (methanol, ethanol, n-propanol, n-butanol, isopropanol, 2-ethoxyethanol or 2-methoxyethanol), an ether (preferably tetrahydrofuran, dioxane, 1,2-dimethoxyethane or diethylene glycol dimethyl ether) or a hydrocarbon such as xylene, toluene, mesitylene, tetralin or decalin. It is also possible to use an excess of the amine $R^9H$ as solvent.

The reaction is carried out at temperatures in the range from 20° C. to the boiling point of the solvent used, and temperatures from 40° to 120° C. are preferred, especially from 40° to 80° C.

It is advantageous, especially with the low-boiling amines, to carry out the reaction under a pressure of inert gas (20–50 bar of $N_2$ or argon) in an autoclave.

It may be advantageous in some cases, especially with the low-boiling amines and in the case of hydroxylamine, to use in place of the free amine a salt of the amine with an organic or inorganic acid, and to liberate the amine therefrom in the reaction mixture with an auxiliary base. Suitable salts are, in particular, the hydrochlorides, hydrobromides, hydrogen sulfates, sulfates or acetates; suitable auxiliary bases are alkali metal and alkaline earth metal carbonates and bicarbonates, such as sodium carbonate, sodium bicarbonate, potassium carbonate, potassium bicarbonate or calcium carbonate, or alkali metal salts of organic acids such as sodium acetate or potassium acetate, or tertiary amines, especially trialkylamines such as triethylamine, diisopropylethylamine, tributylamine or trioctylamine. The reaction is preferably carried out in an alcohol, for example methanol, ethanol, n-propanol, n-butanol, isopropanol, 2-ethoxyethanol or 2-methoxyethanol as solvent, at temperatures from 20° to 120° C., especially from 40° to 100° C., possibly in an autoclave under a pressure of inert gas.

It may be advantageous in some of the processes described above to protect a reactive group which is present in the starting material, especially a hydroxyl group which is not intended to take part in the reaction, with a suitable protective group. Preferred protective groups are those, especially ethers or carbonates, which can be eliminated under mild acidic or neutral conditions or by hydrogenolysis, such as tert-butyl, benzyl, 4-methoxybenzyl, benzhydryl, methoxymethyl, 1-ethoxyethyl or tetrahydropyranyl ethers, silyl ethers such as trimethylsilyl or tert.-butyldimethylsilyl or carbonates such as benzyloxycarbonyl and tert.-butoxycarbonyl derivatives, which are well known from peptide and steroid chemistry.

After the main reaction has taken place, these protective groups can be removed in a generally known manner, for example by treatment with organic acids such as formic acid, acetic acid, trifluoroacetic acid or oxalic acid or a mixture thereof, optionally in the presence of water and/or inert organic solvents such as lower alcohols (for example methanol or ethanol) or cyclic ethers (for example tetrahydrofuran or dioxane) and with liberation of the hydroxyl. Suitable for eliminating silyl protective groups are fluorides such as KF, CsF or $Bu_4NF$. Suitable for eliminating benzyl, benzhydryl, 4-methoxybenzyl or benzyloxycarbonyl protective groups is also hydrogenation in the presence of a suitable catalyst, for example palladium, platinum, platinum oxide or nickel. This reaction is preferably carried out in an organic solvent, especially in a lower alcohol such as methanol or ethanol, or in acetic acid, possibly with the addition of water; under pressures of hydrogen from 1 to 200 bar, preferably from 1 to 100 bar, at temperatures from 20° to 100° C., preferably at 20° to 60° C., especially at room temperature (20°–30° C).

The pure enantiomers of the compounds of the general formula I according to the invention can be obtained not only by specific synthesis by process A from an optically active epoxide of the general formula III but also by racemate resolution of a racemic product of the general formula I. Resolution of the racemates of the compounds of the general formula I according to the invention into the two enantiomers is preferably carried out by chromatographic separation (HPLC) on an optically active support material. Examples of suitable materials are triacetylcellulose, tribenzoylcellulose or silica gel modified with dinitrobenzoyl-phenylglycine (called Perkle phases).

Also suitable for racemic resolution of the compounds of the general formula I, according to the invention, in which $R^4$ is OH is derivatization of this OH group with an optically active carboxylic acid (as ester) or an optionally active isocyanate (as carbamate), followed by chromatographic separation of the resulting diastereomers and finally cleavage of the derivative again. Particularly suitable optically active aids are isocyanates such as dehydroabietyl isocyanate or (R)- or (S)-1-(1-naphthyl)ethyl isocyanate or N-protected natural amino acids such as (S)-N-methanesulfonyl-phenylalanine. The derivatization and the cleavage back are carried out by standard processes familiar to the expert.

This invention further relates to processes for the preparation of the precursors of the general formula III.

The compounds of the general formula III according to the invention are prepared by process Q or R.

Process Q comprises a compound of the general formula V

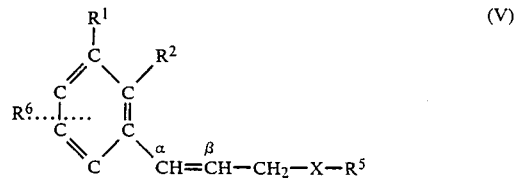

in which the radicals, $R^1$, $R^2$, $R^5$, $R^6$ and X have the same meaning as in formula I being epoxidized. A number of standard processes for the epoxidation are familiar to the expert (see Houben-Weyl, Methoden der organischen Chemie (Methods of Organic Chemistry), volume 6/3, pages 385 et seq.); especially reaction with organic peracids such as peracetic acid, perbenzoic, 3-chloroperbenzoic acid and perphthalic acid. In this, cis-olefins give cis-epoxides, and trans-olefins correspondingly give trans-epoxides.

The preferred embodiment of process Q is reaction of the olefins of the general formula V, especially those in which X is O, with peracetic acid or 3-chloroperbenzoic acid in an inert organic solvent, especially in a chlorinated hydrocarbon such as methylene chloride, chloroform or 1,2-dichloroethane, preferably in the presence of an aqueous buffer solution such as aqueous sodium bicarbonate solution, or phosphate buffer pH 8. The reaction is carried out in a temperature range from −78° to 50° C., preferably from −30° to 30° C., especially from −15° to 10° C.

Another preferred embodiment of process Q is reaction of the olefins of the general formula V with potassium persulfate (KHSO$_5$). This reaction is carried out in analogy to a procedure of Bloch et al. (J. Org. Chem. 50 (9), 1544-45 (1985)) in a mixture of water and a water-miscible organic solvent such as methanol, ethanol or acetone at temperatures from 0° to 80° C., preferably of 20°-50° C., especially from 20° to 30° C.

Process R comprises a compound of the general formula VIII

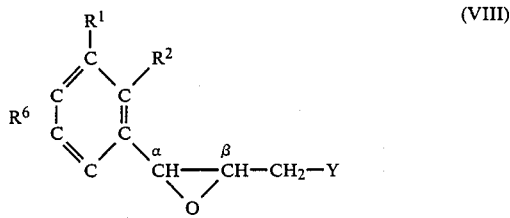

(VIII)

in which the radicals R$^1$, R$^2$ and R$^6$ have the same meaning as in formula I, and Y is a leaving group, especially a sulfonyloxy group such as methanesulfonyloxy, benzenesulfonyloxy, p-toluenesulfonyloxy or trifluoromethanesulfonyloxy, being reacted with a compound of the general formula R$^5$XM in which R$^5$ and X have the same meaning as in formula I, and M denotes hydrogen or an alkali metal.

The reaction is advantageously carried out in an organic solvent such as toluene, tetrahydrofuran, diethyl ether, tert.butyl methyl ether, dimethylformamide, dimethyl sulfoxide or a lower alcohol such as methanol, ethanol, isopropanol or tert.-butanol, in the presence of a base. Suitable bases are alkali metal carbonates, hydroxides, alcoholates or hydrides; the preferred base is sodium hydride.

A particularly favorable variant of process R comprises reacting a compound of the general formula VIII with a compound of the general formula R$^5$XM in which R$^5$ and X have the same meaning as in formula I, and M is an alkali metal, especially sodium, in an inert solvent such as tetrahydrofuran, dimethylformamide or dimethyl sulfoxide. The necessary compounds R$^5$XM can easily be prepared in a separate step from the corresponding compounds R$^5$XH and an alkali metal hydride MH (especially sodium hydride) in an aprotic solvent such as as n-hexane, cyclohexane, toluene or diethyl ether.

The reaction is carried out in a temperature range from −20° C. to the boiling point of the solvent used, preferably in the range 0°-80° C., especially 0°-50° C.

It is possible by process R for the compounds of the general formula III according to the invention, and from these those of the formula I with R$^4$=OH, to be obtained in optically pure form by using a compound of the general formula VIII in optically pure form.

Process R is particularly suitable for the preparation of those compounds of the general formula III, according to the invention, in which X is S.

The precursors of the general formula IV which are necessary for process B can be obtained by reaction of a diol of the general formula X

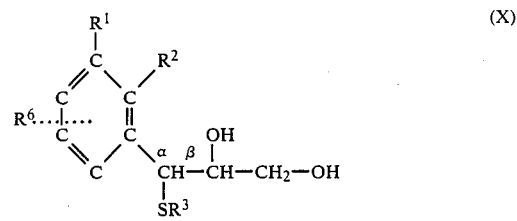

(X)

in which R$^1$, R$^2$, R$^3$ and R$^6$ have the same meaning as in formula I with a sulfonyl chloride or sulfonic anhydride, for example methanesulfonyl chloride, benzenesulfonyl chloride, p-toluenesulfonyl chloride or trifluoromethanesulfonic anhydride, by processes familiar to the expert, for example in pyridine or mixtures of pyridine or triethylamine with an inert organic solvent such as toluene, methylene chloride or ether, at reaction temperatures from −40° to 25° C. (depending on the sulfonic acid derivative).

The compounds of the general formula X are in turn obtained by reaction of an epoxy alcohol of the general formula IX in which the radicals R$^1$, R$^2$ and R$^6$ have the same meaning as in formula I, by reaction with a mercaptan of the general formula R$^3$SH, where R$^3$ has the meaning mentioned for formula I. The reaction is carried out under the conditions mentioned in process A.

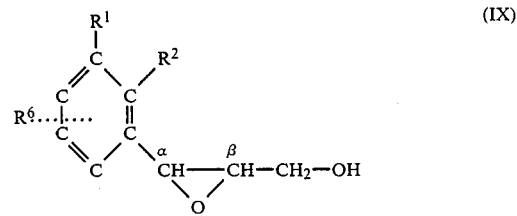

(IX)

The epoxy alcohols of the general formula IX can be obtained by epoxidation of the cinnamyl alcohols of the general formula VIIa (trans isomer) or VIIb (cis isomer). The epoxidation can be carried out in analogy to process P using a peracid; however, particularly suitable in this case is epoxidation with a tertiary alkyl hydroperoxide such as tert.-butyl hydroperoxide or cumene hydroperoxide, in the presence of a metal complex having catalytic activity. Suitable catalysts are vanadyl acetylacetonate, molybdenum hexacarbonyl, dibutyltin oxide or titanium tetraisopropylate (see Houben-Weyl, Methoden der organischen Chemie, volume 4/1a, pages 231 et seq. for a review). The reaction is carried out in an inert organic solvent, especially a saturated or aromatic hydrocarbon or a halogenated hydrocarbon, with toluene or methylene chloride being preferred; the reaction temperature is between 0° C. and the boiling point of the solvent used, and the reaction is preferably carried out at room temperature (20°-30° C.).

The relative configuration of the resulting products IX depends on the geometry of the cinnamyl alcohol used; the trans-epoxy alcohols IXa are formed from the trans-cinnamyl alcohols VIIa and the corresponding cis-epoxy alcohols are formed from the cis-cinnamyl alcohols VIIb.

Particularly suitable for obtaining optically active epoxy alcohols of the general formula IX from the non-chiral cinnamyl alcohols VIIa and VIIb is the SHARPLESS epoxidation (see Houben-Weyl, Methoden der organischen Chemie, volume 4/1a, pages 235-6). This entails the epoxidation being carried out with an alkyl hydroperoxide, preferably t-butyl or cumene hydroperoxide, in the presence of titanium tetraisopropylate as catalyst and (−)- or (+)-tartaric esters as chiral aid. Particularly suitable are dimethyl, diethyl or diisopropyl tartrate, especially diethyl tartrate. The reaction is carried out in an inert organic solvent, especially a saturated or aromatic hydrocarbon or a halogenated hydrocarbon, with toluene or methylene chloride being preferred; the reaction temperature is between −40° C. and the boiling point of the solvent used, and the reaction is preferably carried out in the range from −20° C. to room temperature (20°-30° C.).

The molar ratio of the reactants is typically about 1:2:1:1 (cinnamyl alcohol : hydroperoxide : Ti(O$^i$Pr)$_4$ : tartaric ester). It is possible by addition of activated molecular sieves to reduce markedly the quantity of catalyst and tartaric ester required (see B. Sharpless et al., J. Org. Chem. 51, 1922 (1986)), in which case the typical ratio of the components is about 1:1.5-2:0.05:0.05-0.075.

The absolute configuration of the resulting product IX at C-α depends on the geometry of the cinnamyl alcohol used (as a consequence of the convention for the R,S nomenclature), but that at C-β depends only on the direction of rotation of the tartaric ester used. Experience has shown that use of L-(+)-tartaric esters gives products with the β-(S) configuration, and use of D-(−)-tartaric esters correspondingyl gives products with the β-(R) configuration.

Further details of the preparation of the cinnamyl alcohols VIIa and VIIb will be given hereinafter.

Scheme 2

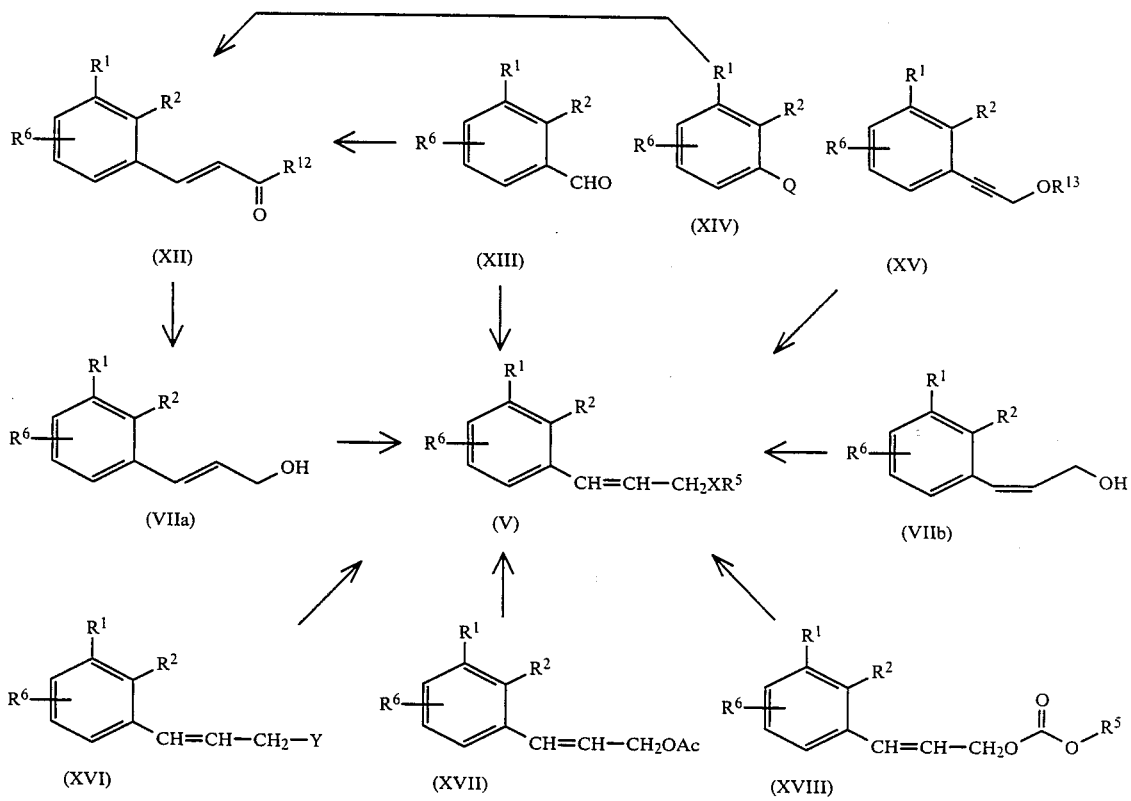

Those olefins of the general formula V which are not already known can be prepared in various ways, with the preferred way being dependent on the nature of the radicals X and R$^5$ and on the desired geometry of the double bond (cis or trans). Scheme 2 provides a summary.

One process for preparing the intermediates of the general formula V in which X is SO or SO$_2$ comprises oxidation of the corresponding compounds of the same general formula V in which X is S. Suitable oxidizing agents are organic peracids such as peracetic acid, m-chloroperbenzoic acid or perphthalic acid, hydrogen peroxide in acetic acid or acetic anhydride, as well as inorganic oxidizing agents such as sodium perborate, KHSO$_5$, NaIO$_4$, NaOCl and NaClO$_2$, which are preferably used in aqueous systems such as mixtures of water with methanol, acetone or acetic acid.

One process for preparing the intermediates of the general formula V in which X is O comprises O-alkylation of a cinnamyl alcohol of the general formula VIIa (trans-isomer) or VIIb (cis-isomer) in which the radicals $R^1$, $R^2$ and $R^6$ have the meaning mentioned for formula I, using a compound of the formula $R^5Y$, where $R^5$ has the meaning mentioned for formula I but cannot be phenyl, and Y is a leaving group such as Cl, Br, I or $OSO_2W$ ($W=CH_3$, Ph, tolyl, $CF_3$ or $OR^7$). The reaction is carried out under the conditions mentioned for process C. This process is unsuitable for preparing those compounds of the formula V in which $R^5$ is a (possibly substituted) phenyl radical; in the preparation of compounds of the formula V in which $R^5$ is $C_2$-$C_4$-hydroxyalkyl, it is expedient to use in place of the free hydroxy compound a protected derivative, for example a tetrahydropyranyl ether, and then to eliminate the protective group in a subsequent step.

Those trans-cinnamyl alcohols of the general formula VIIa which are not known can be prepared by reduction of the carbonyl compounds of the general formula XII in which $R^1$, $R^2$ and $R^6$ have the meaning mentioned for formula I, and $R^{12}$ is H, methoxy or ethoxy, by methods known in principle. Suitable reducing agents are complex hydrides such as sodium borohydride, lithium borohydride, lithium aluminum hydride, but especially diisobutylaluminum hydride or aluminum hydride. The reaction is advantageously carried out in an inert organic solvent such as tetrahydrofuran, diethyl ether, tert.butyl methyl ether, toluene or methylene chloride.

The reaction is carried out at temperatures from $-20°$ C. to the boiling point of the solvent used. A temperature range from $0°$ to $100°$ C. is preferred, especially from $0°$ to $60°$ C.

Those carbonyl compounds of the general formula XII which are not already known can be obtained by standard processes, which are familiar to the expert, from the benzaldehydes of the general formula XIII in which $R^1$, $R^2$ and $R^6$ have the meaning mentioned for formula I. Particularly suitable for this is reaction of the aldehydes XIII with Wittig reagents such as $Ph_3P=CH$—$COR^{12}$, in which $R^{12}$ has the meaning mentioned for formula XII, or with phosphonates such as triethyl phosphonoacetate or trimethyl phosphonoacetate in the presence of a base such as potassium carbonate, sodium carbonate, a sodium or potassium alcoholate, sodium or potassium hydride or sodium or potassium hydroxide, the latter especially in the presence of a phase-transfer catalyst.

Another process for preparing the precursors of the general formula XII in which $R^{12}$ denotes methoxy or ethoxy comprises reacting a benzaldehyde of the general formula XIII with monomethyl or monoethyl malonate under the conditions of the Knoevenagel reaction which is well known to the expert.

A process, which is likewise favorable in some cases, for preparing the precursors of the general formula XII in which $R^{12}$ denotes methoxy or ethoxy comprises esterification of the corresponding carboxylic acids (XII, $R^{12}=OH$) by a standard process known to the expert. Very suitable for this is, especially, alkylating esterification as has been described, for example, in process J. Those carboxylic acids which are not known are in turn obtainable by Knoevenagel condensation of the aldehydes XIII with malonic acid. They are also produced in some cases when an attempt is made to prepare the esters XII ($R^{12}=OMe$ or OEt) by the Horner reaction (reaction of the aldehydes XIII with triethyl or trimethyl phosphonoacetate) under phase-transfer conditions (toluene/50% strength sodium hydroxide solution/tetrabutylammonium bromide or another phase-transfer catalyst), and they can also be obtained specifically in this way if the reaction mixture is, before working up, diluted with methanol or ethanol and left to stir for a further few hours. Although this route via the carboxylic acids is in principle a roundabout route, it is nevertheless worthwhile in some cases, because it is often easier to purify the carboxylic acids than their esters.

Another process for preparing the precursors of the general formula XII in which $R^{12}$ denotes methoxy or ethoxy comprises reacting a compound of the general formula XIV in which $R^1$, $R^2$ and $R^6$ have the meaning mentioned for formula I, and Q is a halogen radical, especially bromine or iodine, with methyl or ethyl acrylate in the presence of catalytic quantities of a palladium(O) complex or a palladium(II) salt (palladium acetate or palladium chloride) and a base (Heck reaction, see Organic Reactions vol. 27, pages 345 et seq. for a review).

Finally, the trans-cinnamyl alcohols VIIa can also be obtained by reduction of the corresponding propargyl alcohols XV ($R^{13}=H$) with $LiAlH_4$ (see Houben-Weyl, Methoden der organischen Chemie, volume 5/2a, pages 707 et seq.).

The propargyl alcohols XV ($R^{13}=H$) can also be converted into the cis-cinnamyl alcohols VIIb by catalytic hydrogenation on suitable metal catalysts, especially so-called Lindlar catalysts (see Houben-Weyl, Methoden der organischen Chemie, vol. 5/2a, pages 696 et seq.) or by hydroboronation with sterically hindered boranes such as dicyclohexylborane, disiamylborane, thexylborane or 9-borabicyclononane (see Houben-Weyl, Methoden der organischen Chemie, vol. 5/2a, pages 703 et seq.).

It is also possible analogously to obtain directly the precursors of the general formula V in which X is O, and the double bond has the cis configuration, from the propargyl ethers XV in which $R^1$, $R^2$ and $R^6$ have the same meaning as in formula I, and $R^{13}$ has the same meaning as $R^5$ in formula I, by hydroboronation or catalytic hydrogenation.

The compounds of the general formula XV can in turn be obtained from the compounds of the general formula XIV in which $R^1$, $R^2$ and $R^6$ have the meaning mentioned for formula I, and Q is a halogen radical, especially bromine or iodine, or a radical $OSO_2R^f$, where $R^f$ is a perfluorinated alkyl radical such as trifluoromethyl or nonaflyl (nonafluorobutyl), and an acetylene of the general formula XIX in which $R^{13}$ either is H or has the same meaning as $R^5$ in formula I, under the conditions of the Heck reaction with the addition of catalytic quantities of CuI (see Sakamoto et al., Chem. Pharm. Bull. 341, 2754-59 (1986)).

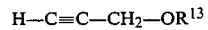

$$H-C\equiv C-CH_2-OR^{13} \qquad (XIX)$$

Another method for preparing the precursors V comprises reacting a compound of the general formula XVI in which $R^1$, $R^2$ and $R^6$ have the same meaning as in formula I, and Y is a leaving group such as Cl, Br, I or $OSO_2W$ ($W=CH_3$, Ph, tolyl or $CF_3$), with a compound $R^5XH$ in which $R^5$ and X have the same meaning as in formula I. The reaction is advantageously carried out in an inert organic solvent such as toluene, tetrahydrofuran, diethyl ether, tert.butyl methyl ether, dimethylformamide or dimethyl sulfoxide—and in the case where X=S it is possible to use lower alcohols such as methanol, ethanol, isopropanol or tert.-butanol—in the presence of a base. Suitable bases in the case where X=O are particularly strong bases such as potassium tert.butylate, sodium hydride or lithium alkyls (preferably n-butyllithium), and in the case where X=S it is possible to use alkali metal alcoholates such as sodium methylate or sodium ethylate, especially when the corresponding alcohol is used as solvent. The preferred base is sodium hydride, and preferred solvents are tetrahydrofuran and dimethylformamide.

The precursors XVI can easily be obtained from the corresponding alcohols VIIa or VIIb by processes familiar to the expert. Examples which may be mentioned are the reaction of VIIa or VIIb with thionyl chloride in an inert solvent, such as methylene chloride, ether or toluene, to give compounds XVI in which Y is Cl; the reaction with phosphorus tribromide (without solvent or in an inert solvent such as ether) to give the compounds XVI in which Y is Br; the reaction with methanesulfonyl chloride or p-toluenesulfonyl chloride in pyridine or mixtures of pyridine or triethylamine with an inert solvent such as toluene or methylene chloride to give the compounds XVI in which Y is methanesulfonyloxy or p-toluenesulfonyloxy.

Another process for preparing the precursors of the general formula V, especially those in which X is O, comprises reacting the cinnamyl acetates XVII with a trialkyltin or triphenyltin alcoholate of the general formula XX, $$R_3^{14}Sn—OR^5 \qquad (XX)$$

in which $R^{14}$ is a lower unbranched alkyl radical, especially methyl or butyl, or a phenyl radical, and $R^5$ has the same meaning as in formula I. This reaction is carried out by the general procedure of E. Keinan et al. (J. Org. Chem. 50, 3558–66 (1985)) in the presence of catalytic quantities of a palladium(O) complex such as Pd[PPh$_3$]$_4$.

Those of the required tin alcoholates XX which are not already known can easily be prepared by reaction of an alkali metal alcoholate R$^5$OM (M=Li, Na or K) with a triorganyltin chloride R$_3^{14}$SnCl. It is also possible in principle for other cinnamyl esters, for example propionates, butyrates or benzoates, to be used in place of the cinnamyl acetates XVII. These compounds can be obtained, just like the acetates XVII, very simply by reacting the cinnamyl alcohols VIIa or VIIb with the appropriate acyl chloride or anhydride by standard processes known to the expert (see Houben-Weyl, Methoden der organischen Chemie, 8, 543 et seq.).

Another method for preparing the intermediates V in which X is O comprises reacting a cinnamyl carbonate of the general formula XVII in which R$^1$, R$^2$, R$^5$ and R$^6$ have the same meaning as in formula I in the presence of a catalytic quantity of a palladium(O) complex such as, for example, Pd[PPh$_3$]$_4$, which can also be prepared in situ from a palladium salt such as PdCl$_2$ or Pd(OAc)$_2$ and triarylphosphine such as PPh$_3$. The reaction is carried out in analogy to a procedure of F. Guibe et al. (Tetrahedron Letters 22, 3591–4 (1981) by heating the reactants in an inert solvent such as toluene.

The cinnamyl carbonates XVIII are easily obtained from the cinnamyl alcohols VIIa or VIIb by acylation, under standard conditions (pyridine or pyridine/methylene chloride, 20° C. →RT), with the chloroformic esters of the general formula XXI in which R$^5$ has the same meaning as in formula I.

$$\underset{\text{Cl}—\overset{\overset{\displaystyle O}{\|}}{C}—OR^5}{} \qquad (XXI)$$

Those chloroformic esters XXI which are not known can in turn be prepared from the alcohols R$^5$OH in which R$^5$ has the same meaning as in formula I and phosgene (see Houben-Weyl, Methoden der organischen Chemie, E4, 15 et seq.).

Another method for preparing the intermediates of the general formula V in which X is O, R$^1$, R$^2$ and R$^6$ have the same meaning as in formula I, and R$^5$ is a Cl$_1$–C$_4$-alkyl, alkoxyalkyl or hydroxyalkyl radical, comprises reacting an aldehyde of the general formula XIII in which R$^1$, R$^2$ and R$^6$ have the same meaning as in formula I in the presence of a base with a phosphonium salt of the general formula XXII or XXIII, $$[Ar_3P—CH_2CH_2—OH]^+B^- \qquad (XXII)$$

$$[Ar_3P—CH=CH_2]^+B^- \qquad (XXIII)$$

where Ar is an aromatic radical, preferably phenyl and B$^-$ is an anion such as Cl$^-$, Br$^-$or I$^-$. The reaction is carried out in the alcohol R$^5$OH as solvent, and suitable bases are alkali metal hydroxides and carbonates, as well as the alcoholates obtained from the alcohols R$^5$OH, for example by reaction with an alkali metal or alkali metal hydride. "Alkali metal" in the above context denotes, in particular, potassium or sodium; the preferred base is potassium carbonate. The reaction is carried out at temperatures from 20° C. to the boiling point of the alcohol used, preferably between 40° and 150° C., especially between 60° and 120° C. The trans-isomers are preferentially formed in the reaction. For an analogous procedure, see F. Cheik-Rouhou et al., Synth. Commun. 16 [14], 1739–43 (1986)).

The starting materials of the general formula VIII required for process R for preparing the compounds of the general formula III according to the invention can be obtained by standard processes familiar to the expert from the epoxy alcohols of the general formula IX in which the radicals R$^1$, R$^2$ and R$^6$ have the same meaning as in formula I, by reacting with a sulfonyl chloride or sulfonic anhydride, for example methanesulfonyl chloride, benzenesulfonyl chloride, p-toluenesulfonyl chloride or trifluoromethanesulfonic anhydride, in pyridine or mixtures of pyridine or triethylamine with an inert organic solvent such as toluene, methylene chloride or ether, at reaction temperatures from −40° to 25° C. (depending on the sulfonic acid derivative).

As is evident from scheme 2, either the aldehydes XIII or the aryl halides XIV (Q=Br or I) are the common precursor for the various routes which lead via the compounds VIIa, VIIb or V to the compounds of the formulae I and III according to the invention. Quite a few compounds of the formulae XIII and XIV are already known, and others can be prepared by various processes, the choice of which is mainly determined by the nature of the radicals R$^1$, R$^2$ and R$^6$.

Compounds of the general formula XIII in which the radical R$^2$ is an ether group (OZ) can be obtained by alkylation of the corresponding 2-formylphenols XXIV

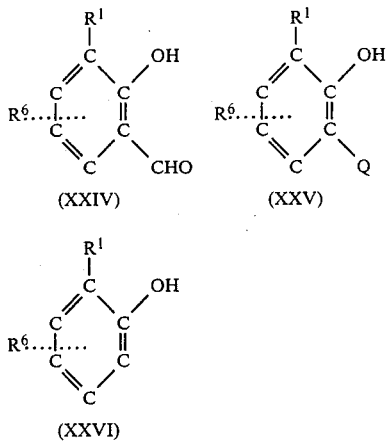

(XXIV)   (XXV)

(XXVI)

in which $R^1$ and $R^6$ have the same meaning as in formula I, with a compound $R^{15}Y$, where $R^{15}$ has the same meaning as the radical Z in formula I but cannot be phenyl; Y is a leaving group such as Cl, Br, $CH_3SO_2O$, $PhSO_2O$, p-tolyl$SO_2O$, $CF_3SO_2O$ or, especially when $R^{15}$ is a lower alkyl radical, a radical $R^{15}OSO_2O$. The alkylation can be carried out by standard processes (see Houben-Weyl, Methoden der organischen Chemie, vol. 6/3, pages 385 et seq.). Those compounds $R^{15}Y$ which are not known can easily be prepared by standard processes familiar to the expert, for example from the corresponding alcohols $R^{15}OH$. Suitable for preparing the compounds of the general formula XXIV is formylation of the corresponding phenols XXVI, for which many methods are known. If the radical $R^6$ occupies the position para to the OH group, especially suitable is Vilsmeier-Haack formylation (see Houben-Weyl, Methoden der organischen Chemie, volume E3, pages 36 et seq.), otherwise it is best to use the ortho-selective formylation with formaldehyde by the method of Casiraghi et al. (see Houben-Weyl, Methoden der organischen Chemie, volume E3, page 103).

Suitable for the preparation of the precursors XIV is correspondingly the alkylation of 2-halogenophenols of the general formula XXV with a compound $R^{15}Y$, where the radicals $R^1$, $R^6$ and $R^{15}$ have the abovementioned meaning; Q is Br or I. In turn, the compounds XXV can be obtained by bromination or iodination of the phenols XXVI by known processes.

Another method for preparing the precursors of the general formula XIII is the formylation of a compound of the general formula XXVII in which the radicals $R^1$, $R^2$ and $R^6$ have the meaning mentioned for formula I, by one of the many known standard processes (see Houben-Weyl, Methoden der organischen Chemie, volume E3, pages 16 et seq.). These methods are applicable especially when the radical $R^2$ is an ether radical (OZ) and the radical $R^6$ is in the position para to $R^2$.

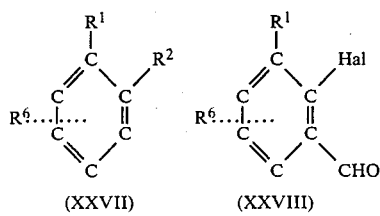

(XXVII)   (XXVIII)

Alternatively, it is also possible to prepare from a compound of the general formula XIV in which Q denotes a halogen atom, especially Br or I, an organolithium or organomagnesium compound by halogen-/metal exchange, and then to formylate the latter by reaction with a formic acid derivative. Standard processes also exist for this reaction (see Houben-Weyl, Methoden der organischen Chemie, volume E3, pages 115 et seq.).

Suitable for the preparation of those precursors of the general formula XIII in which the radical $R^2$ is an alkyl, alkenyl or alkynyl group, even one substituted with phenyl, is the reaction of a 2-halogenobenzaldehyde of the general formula XXVIII in which $R^1$ and $R^6$ have the meaning mentioned for formula I, and Hal symbolizes a bromine or iodine atom, with a compound of the general formulae XXIX, XXX or XXI, in which $R^{16}$ symbolizes an alkyl or phenylalkyl radical, and $R^{17}$ symbolizes a linear $C_1$-$C_4$-alkyl radical, $$HC\equiv C-R^{16} \qquad (XXIX)$$

$$H_2C=CH-R^{16} \qquad (XXX)$$

$$R_3{}^{17}Sn-CH=CH-R^{16} \qquad (XXXI)$$

in the presence of a palladium or nickel complex (Heck reaction and variants thereof, for reviews, see: Organic Reactions, volume 27, pages 345 et seq.; J. Tsuji, "Organic Synthesis with Palladium Compounds", Springer-Verlag 1980; Angew. Chemie, 98, 504–19 (1986)). It is possible to obtain from the compounds of the general formula XIII which have been prepared in this way, and in which $R^2$ is an unsaturated radical, the corresponding saturated compounds by catalytic hydrogenation.

Those compounds of the general formula I according to the invention which contain a carboxyl group can form salts with inorganic or organic bases. The present invention therefore also relates to such salts. Salts with inorganic bases are preferred, especially the physiologically acceptable alkali metal salts, in particular sodium and potassium salts.

The compounds of the general formula I according to the invention have valuable pharmacological properties; in particular, they antagonize the action of the leukotrienes.

The leukotriene-antagonistic action of the substances of the general formula I according to the invention is determined by the inhibition of the leukotriene-induced contraction of strips of guinea pig lung. The method which is used is a modification of the tests described by Foreman, Shelly and Weber (Arch. Int. Pharmacodyn. 278, 193–206 (1985)).

Guinea pigs are sacrificed by an overdose of ether. The thoracic cavity is opened; the lungs are removed and cut into strips 5 cm long, which are stored in physiological saline. For the measurement, the strips of lung are placed in an organ bath filled with Ringer's solution which is equilibrated at 37° C. and through which carbogen ($O_2/CO_2$ 95:5 parts by volume) is passed. The strips are left to equilibrate under a load of 0.5–1 g for 30–60 minutes. The strips of lung are pretreated with indomethacin ($10^{-6}$ g/ml of bath liquid) before the test starts.

The contraction is induced by adding $LTC_4$, $LTD_4$ or $LTE_4$ in a concentration of 3 ng/ml of bath liquid. The test substances are administered therapeutically into the bath, after the maximum contraction plateau has been reached, in several concentrations and at time intervals of 10 minutes. 6-12 strips of lung are used for each concentration of the test substances.

The concentrations of the test substances at which the contraction is reduced by 50% ($IC_{50}$) are indicated in μg/ml.

The results of the pharmacological tests on the following compounds are detailed hereinafter by way of example:

Compound A: Methyl (5RS,6SR)-5-hydroxy-6-(3-methoxyphenylthio)-6-phenyl-3-oxahexanoate Compound B: Methyl (5RS,6SR)-5-hydroxy-6-(3-methoxyphenylthio)-6-phenyl-3-thiahexanoate Compound C: Methyl (5 S,6 R)(−)-5-hydroxy-6-(3-methoxyphenylthio)-6-phenyl-3-thiahexanoate Compound D: Methyl (5RS,6SR)-5-hydroxy-6-phenyl-3-oxa-7-thiadecanoate Compound E: Methyl (5RS,6SR)-5-hydroxy-6-phenyl-3,7-dithiadecanoate

| Compound | $IC_{50}$ [μg/ml] versus | | |
|---|---|---|---|
| | $LTC_4$ | $LTD_4$ | $LTE_4$ |
| A | 0.6 | 0.3 | 1.0 |
| B | 0.6-1.0 | 0.6 | 1.0 |
| C | 0.3-0.6 | 0.1 | 0.3-0.6 |
| D | >10 | 0.5 | >10 |
| E | 6.0 | 0.6-1.0 | 6-10 |

The compounds according to the invention are, by reason of their pharmacological properties, suitable for the treatment of allergic and inflammatory disorders such as asthma, allergic skin reactions, psoriasis, ulcerative colitis or rheumatoid arthritis, as well as shock.

Hence the invention also relates to the use of the compounds of the formula I according to the invention for the treatment and prophylaxis of the disorders listed above.

The invention furthermore embraces the use of the compounds according to the invention for the preparation of pharmaceuticals used for the treatment and prophylaxis of the abovementioned disorders.

The invention further relates to pharmaceuticals which contain one or more compounds of the general formula I according to the invention, and/or their pharmacologically tolerated salts.

The pharmaceuticals are prepared by processes known per se and familiar to the expert. The pharmacologically active compounds (=active substance) according to the invention are used as pharmaceuticals either as such or, preferably, in combination with suitable pharmaceutical auxiliaries in the form of tablets, coated tablets, capsules, suppositories, emulsions, suspensions, creams, ointments, granules, powders or solutions, with the content of active substance advantageously being between 0.1 and 95%.

The particular auxiliaries suitable for the desired pharmaceutical formulation are familiar to the expert on the basis of his expert knowledge. Apart from solvents, gelling agents, suppository bases, tablet auxiliaries and other active substance vehicles, it is possible to use, for example, antioxidants, dispersing agents, emulsifiers, antifoam agents, flavorings, preservatives, solubilizers or colorants.

The active substances can be administered topically, orally, parenterally, intravenously, rectally or by inhalation, with the preferred mode of administration being dependent on the disorder to be treated.

For a form for oral administration, the active compounds are mixed with the additives suitable for this purpose, such as excipients, stabilizers or inert diluents, and converted by the customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose or starch, especially corn starch. In this connection, preparation can be effected both as dry and as wet granules. Examples of suitable oily excipients or solvents are vegetable or animal oils, such as sunflower oil or fish liver oil.

For subcutaneous or intravenous administration, the active compounds, or the physiologically tolerated salts thereof, are converted into a solution, suspension or emulsion, if desired with the substances customary for this purpose, such as solubilizers, emulsifiers or other auxiliaries. Examples of suitable solvents are water, physiological saline or alcohols, for example ethanol, propanol and glycerol, as well as sugar solutions such as glucose or mannitol solutions, or else a mixture of the various solvents mentioned.

Pharmaceutical products for topical and local use are, for example for treating the skin, lotions and creams which contain a liquid or semi-solid oil-in-water or water-in-oil emulsion, and ointments (which preferably contain a preservative). Suitable for treating the eyes are eyedrops which contain the active compound in aqueous or oily solution. Suitable for treatment of the nose are aerosols and sprays, similar to those described hereinafter for treating the airways, coarse powders which are administered by rapid inhalation through the nostrils, and in particular nose drops which contain the active compounds in aqueous or oily solution.

Examples of pharmaceutical formulations suitable for administration in the form of aerosols or sprays are solutions, suspensions or emulsions of the active substance of the general formula I according to the invention in a pharmaceutically acceptable solvent such as, especially, ethanol or water, or a mixture of such solvents. The formulation can, where required, also contain other pharmaceutical auxiliaries such as surfactants, emulsifiers and stabilizers, as well as a propellant gas. A formulation of this type normally contains the active substance in a concentration of about 0.1 to 10, in particular of about 0.3 to 3, % by weight.

The dosage of the active substance of the formula I which is to be administered, and the frequency of administration, depend on the strength of action and duration of action of the compound used; as well as on the nature and severity of the disorder which is to be treated and on the sex, age, weight and individual response of the mammal which is to be treated. On average, the recommended daily dose of a compound of the formula I according to the invention would probably be, for a mammal weighing about 75 kg—primarily a human—in the range from about 10 to 500 mg, preferably between about 25 and 250 mg, it being possible for administration to take place in several doses a day as required.

The examples which follow are intended to illustrate the present invention without, however, restricting its scope.

Rf values were determined on precoated silica gel plates (5×10 cm, layer thickness 0.25 mm, silica gel 60 $F_{256}$) from Riedel de Haen. The stated solvent ratios are ratios by volume. The following are stated for NMR spectra: measurement frequency in MHz, solvent, chemical shift for each signal in ppm (relative to tetramethylsilane as standard), multiplicity, any coupling constants in Hz, and number of protons from the integration. Multiplicities are specified by the following abbreviations: s=singlet, d=doublet, t=triplet, q=quartet, m=multiplet, AB=AB system; more complicated signals are indicated by combination of the letters, for example dt=doublet of triplets; broad signals are indicated by addition of "br".

The progress of the reactions was generally followed by thin-layer chromatography; reaction times are therefore stated only by way of example. Solutions were concentrated using a rotary evaporator under a pressure of 1-200 torr and at bath temperatures of 20°-80° C., depending on the solvent.

Where no melting point is given, the relevent compound is a liquid.

EXAMPLE 1

Methyl (5RS,6SR)-5-hydroxy-6-(3-methoxyphenylthio)-6-phenyl-3-oxahexanoate

Stage 1: (E)-6-phenyl-3-oxahex-5-enoic acid 0.1 mol (13.4 g) of trans-cinnamyl alcohol and 0.1 mol (13.9 g) of bromoacetic acid are dissolved in 100 ml of dry tetrahydrofuran. A total of 0.3 mol of NaH (13.5 g of a 55% strength suspension in mineral oil) is added in portions to the solution while stirring and excluding moisture. The mixture is then boiled for 6 h. The solution is poured cautiously into water, and the mixture is acidified to pH 1-2 with 2N hydrochloric and extracted with ether. For purification, the ethereal extract is reextracted with saturated $NaHCO_3$ solution, and the aqueous phase is acidified to pH 1-2 and again extracted with either. The ethereal extract is dried over $Na_2SO_4$ and evaporated in vacuo. The residue is recrystallized from diisopropyl ether/petroleum ether (1:1) with the addition of a little active charcoal.

White solid, melting point 73°-74° C. Rf=0.39 ($CH_2Cl_2$)

$^1$H-NMR (60 MHz, $CDCl_3$, δ in ppm): 4.13 (s, 2H), 4.21 (d, 5-6 Hz, 2H), 5.9-6.7 (m, 2H), 7.0-7.4 (m, 5H), 10.13 (s, 1H)

Stage 2: Methyl (E)-6-phenyl-3-oxahex-5-enoate 0.36 mol (70 g) of stage 1 are dissolved in 700 ml of methanol, and 2 ml of concentrated $H_2SO_4$ are added. The mixture is stirred at room temperature for 24 h and then 50 g of solid $NaHCO_3$ are added, after which the solution is stirred for 1 h and then filtered. The filtrate is concentrated, the residue is taken up in ether, and the solution is washed with saturated $NaHCO_3$ solution, dried ($MgSO_4$) and concentrated. The product is purified by distillation in vacuo.

Colorless oil boiling point: 124°-125° C./0.25 mm Rf=0.57 ($CH_2Cl_2$)

$^1$H-NMR (60 MHz, $CDCl_3$, δ in ppm): 3.70 (s, 3H), 4.08 (s, 2H), 4.18 (d, 5-6 Hz, 2H), 5.9-6.7 (m, 2H), 7.0-7.4 (m, 5H)

Stage 3: Methyl trans-5,6-epoxy-6-phenyl-3-oxahexanoate

A solution of 0.14 mol (29 g of 85% pure) of m-chloroperbenzoic acid in 500 ml of methylene chloride is added dropwise to 0.12 mol (25 g) of stage 2 and 10 g of $NaHCO_3$ in 300 ml of methylene chloride at 0°, and the mixture is then left to stir at room temperature for 5 h. The solution is then extracted with saturated $NaHCO_3$ and $Na_2SO_3$ solution and dried over $MgSO_4$, and the solvent is removed by distillation in vacuo. The remaining oil can be reacted further without purification.

Rf=0.22 (cyclohexane/ethyl acetate 4:1) $^1$H-NMR (270 MHz, $CDCl_3$, δ in ppm): 3.2 (m, 1H), 3.64 (d br, 12 Hz, 1H), 3.7 (s, 3H), 3.75 (d, 3 Hz, 1H), 3.9 (d br, 12 Hz, 1H), 4.18 (s, 2H), 7.2-7.35 (m, 5H)

Stage 4: Methyl 5(RS),6(SR)-5-hydroxy-6-(3-methoxyphenylthio)-6-phenyl-3-oxahexanoate 9 mmol (2 g) of stage 3 and 14 mmol (1.96 g) of 3-methoxythiophenol are dissolved in 5 ml of tetrahydrofuran (abs.), 1 ml of triethylamine is added, and the mixture is stirred under nitrogen at 50° C. for 6 h. The solution is then concentrated, the residue is taken up in ether, and the solution is washed 2×with 30 ml of 1N sodium hydroxide solution, dried over $MgSO_4$ and concentrated. The residue is purified by column chromatography on silica gel (35–70 μm, mobile phase cyclohexane:ethyl acetate 2:1, 1.5 bar). An oil is obtained.

$^1$H-NMR (270 MHz, $CDCl_3$, δ in ppm): 2.50 (s br, 1H), 3.55 (dd, $J_1$=10 Hz), 3.75 (m, 1H), 3.70 (s, 3H), 3.75 (s, 3H), 4.08 (s, 2H), 4.20 (m, 1H), 4.39 (d, 6 Hz, 1H), 6.7–7.4 (m, 9H)

In analogy to Example 1, stage 4, the following compounds are obtained by reaction of methyl trans-5,6-epoxy-6-phenyl-3-oxahexanoate (Example 1, stage 3) with the appropriate thiophenols:

EXAMPLE 2

Methyl 5(RS),6(SR)-5-hydroxy-6-(2-naphthylthio)-6-phenyl-3-oxahexanoate

Rf=0.40 (cyclohexane:ethyl acetate 4:1) $^1$H-NMR (60 MHz, $CDCl_3$, δ in ppm): 2.93 (m, 1H), 3.3–3.8 (m)+3.68 (s) Σ5H, 4.0 (s, 2H), 4.1–4.3 (m, 1H), 4.37 (d, 6 Hz, 1H), 7.0–7.8 (12H)

EXAMPLE 3

Methyl 5(RS)6(SR)-5-hydroxy-6-(3-methylphenylthio)-6-phenyl-3-oxahexanoate

Rf=0.41 (cyclohexane:ethyl acetate 1:1) $^1$H-NMR (270 MHz, $CDCl_3$, δ in ppm): 4.17 (s, 2H), 4.22 (d, 7 Hz, 1H)

EXAMPLE 4

Methyl 5(RS),6(SR)-5-hydroxy-6-(2methylphenylthio)-6-phenyl-3-oxahexanoate $^1$H-NMR (60 MHz, $CDCl_3$, δ in ppm): 2.29 (s, 3H), 2.87 (s, br, 1H), 3.3–3.8 (m)+3.67 (s) Σ5H, 4.00 (s, 2H), 4.16 (m, 2H), 6.8–7.4 (m, 9H)

EXAMPLE 5

Methyl 5(RS),6(SR)-5-hydroxy-6-(3-aminophenylthio)-6-phenyl-3-oxahexanoate

Rf=0.15 (cyclohexane:ethyl acetate 1:1)

$^1$H-NMR (60 MHz, $CDCl_3$, δ in ppm): 3.20 (s br, 3H), 3.3–3.6 (m, 2H), 3.67 (s, 3H), 3.98 (s, 2H), 4.0–4.3 (m, 2H), 6.2–7.2 (m)+7.23 (s br) Σ9H

EXAMPLE 6

Methyl 5(RS),6(SR)-5-hydroxy-6-(4fluorophenylthio)-6-phenyl-3-oxahexanoate

Rf=0.38 (cyclohexane:ethyl acetate 1:1) $^1$H-NMR (270 MHz, $CDCl_3$, δ in ppm): 2.63 (s, 1H), 3.4–3.8

(m)+3.70 (s) Σ5H, 4.02 (s, 2H), 4.1–4.3 (m, 2H), 7.77 (t, 9 Hz, 2H), 7.20 (s+t, 7H)

EXAMPLE 7

Methyl 5(RS)6(SR)-5-hydroxy-6-(2-aminophenylthio)-6-phenyl-3-oxahexanoate
Rf=0.25 (cyclohexane:ethyl acetate 1:1) $^1$H-NMR (270 MHz, CDCl$_3$, δ in ppm): 4.03 (s, 2H), 4.17 (m, 1H)

EXAMPLE 8

Methyl 5(RS),6(SR)-5-hydroxy-6-(4-methoxyphenylthio)-6-phenyl-3-oxahexanoate
Rf=0.26 (cyclohexane:ethyl acetate 1:1) $^1$H-NMR (60 MHz, CDCl$_3$, δ in ppm): 2.92 (s br, 1H), 3.5–3.9 (m)+3.68 (s)+3.73 (s) Σ8H, 4.02 (s, 2H), 4.1 (m, 2H), 6.63 (d, 9 Hz, 2H), 7.15 (d, 9 Hz)+7.18 (s) Σ7H

EXAMPLE 9

Methyl 5(RS),6(SR)-5-hydroxy-6-(2-methoxyphenylthio)-6-phenyl-3-oxahexanoate
Rf=0.29 (cyclohexane:ethyl acetate 1:1) $^1$H-NMR (60 MHz, CDCl$_3$, δ in ppm): 3.1–3.3 (m, 1H), 3.4–3.6 (m, 2H), 3.67 (s, 3H), 3.84 (s, 3H), 3.95 (s, 2H), 3.8–4.2 (m, 1H), 4.3 (d, 5 Hz, 1H), 6.6–6.9 (m, 2H), 7.0–7.4 (m, 7H).

EXAMPLE 10

Dimethyl 5(RS),6(SR)-5-hydroxy-6-phenyl-3-oxa-7-thianonanedioate
4 mmol (0.9 g) of Example 1, stage 3, and 12 mmol (1.1 ml) of methyl thioglycolate are dissolved in 10 ml of tetrahydrofuran (abs.), 2.2 ml of triethylamine are added, and the mixture is stirred under nitrogen at room temperature for 40 h. The solution is then concentrated. The residue is purified by column chromatography on silica gel (35–70 μm, mobile phase cyclohexane:ethyl acetate 2:1, 1.5 bar). An oil is obtained.
Rf=0.67 (cyclohexane:ethyl acetate 4:1) $^1$H-NMR (270 MHz, CDCl$_3$, δ in ppm): 2.4 (s br, 1H), 3.1 (AB-d, 2H), 3.55 (s, 3H), 3.7 (s, 3H), 3.5–3.8 (m, 1H), 4.0–4.3 (m, 1H), 4.1 (s, 2H), 7.1–7.5 (m, 5H).

In analogy to Example 10, the following compounds are obtained by reaction of methyl trans-5,6-epoxy-6-phenyl-3-oxahexanoate (Example 1, stage 3) with the appropriate mercaptans:

EXAMPLE 11

Dimethyl 5(RS),6(SR)-5-hydroxy-6-phenyl-3-oxa-7-thiadecanedioate
Rf=0.43 (cyclohexane/ethyl acetate 4:1) $^1$H-NMR (270 MHz, CDCl$_3$, δ in ppm); 2.2 (s br, 1H), 2.4–2.7 (m, 4H), 3.65 (s, 3H), 3.75 (s, 3H), 4.15 (s, 2H), 7.25–7.5 (m, 5H).

EXAMPLE 12

1-Methyl 11-ethyl 5(RS),6(SR)-5-hydroxy-6-phenyl-3-oxa-7-thiaundecanedioate
Rf=0.50 (cyclohexane:ethyl acetate 4:1) $^1$H-NMR (270 MHz, CDCl$_3$, δ in ppm): 1.15 (t, 7 Hz), 1.6–2.5 (m, 6H), 2.4–2.7 (m, 4H), 3.65 (s, 3H), 4.05 (q, 7 Hz, 2H), 4.1 (s, 2H), 7.1–7.5 (m, 5H).

EXAMPLE 13

1-Methyl 12-ethyl 5(RS),6(SR)-5-hydroxy-6-phenyl-3-oxa-7-thiadodecanedioate
Rf=0.51 (cyclohexane:ethyl acetate 4:1) $^1$H-NMR (270 MHz, CDCl$_3$, δ in ppm): 1.15 (t, 7 Hz), 1.3–1.7 (m, 2H), 2.0–2.5 (m, 6H), 2.4–2.7 (m, 4H), 3.7 (s, 3H), 4.08 (q, 7 Hz, 2H), 4.1 (s, 2H), 7.1–7.5 (m, 5H).

EXAMPLE 14

Butyl 5(RS),6(SR)-5-hydroxy-6-(3-methylphenylthio)-6-phenyl-3-oxahexanoate
Stage 1: Butyl (E)-6-phenyl-3-oxahex-5-enoate is obtained in analogy to Example 1, stage 2, by using n-butanol in place of methanol as solvent.
$^1$H-NMR (60 MHz, CDCl$_3$, δ in ppm): 0.92 ("t", 3H), 1.0–1.8 (m, 4H), 4.08 (s, 2H), 4.12 (t, 6–7 Hz, 2H), 4.22 (d, 5 Hz, 2H), 5.9–6.8 (m, 2H), 7.0–7.4 (m, 5H).
Stage 2: Butyl trans-5,6-epoxy-6-phenyl-3-oxahexanoate is obtained in anlogy to Example 1, stage 3, from butyl (E)-6-phenyl-3-oxahex-5-enoate.
$^1$H-NMR (60 MHz, CDCl$_3$, δ in ppm): 0.93 ("t", 3H), 1.1–1.8 (m, 4H), 3.1–3.3 (m, 1H), 3.6–4.0 (m, 3H), 4.10 (t, 6 Hz)+4.13 (s) Σ4H, 7.23 (s, 5H)
Stage 3: Butyl 5(RS),6(SR)-5-hydroxy-6-(3-methylphenylthio)-6-phenyl-3-oxahexanoate is obtained in analogy to Example 1, stage 4, from butyl trans-5,6-epoxy-6-phenyl-3-oxahexanoate and 3-methylthiophenol.
Rf=0.16 (cyclohexane/ethyl acetate 4:1) $^1$H-NMR (60 MHz, CDCl$_3$, δ in ppm): 0.92 ("t", 3H), 1.0–1.7 (m, 4H), 2.27 (s, 3H), 2.9–3.1 (m, 1H), 3.4–3.8 (m, 2H), 4.08 (s)+3.90–4.30 (m) Σ6H, 6.9–7.5 (m, 9H).

EXAMPLE 15

Butyl 5(RS),6(SR)-5-hydroxy-6-(4-methylphenylthio)-6-phenyl-3-oxahexanoate is obtained in analogy to Example 14, stage 3, from butyl trans-5,6-epoxy-6-phenyl-3-oxahexanoate and 4-methylthiophenol.
$^1$H-NMR (60 MHz, CDCl$_3$, δ in ppm): 0.92 ("t", 3H), 1.0–1.7 (m, 4H), 2.30 (s, 3H), 2.97 (m, 1H), 3.4–3.8 (m, 2H), 4.08 (s)+3.9–4.3 (m) Σ6H, 6.9–7.5 (m, 9H).

EXAMPLE 16

Butyl 5(RS),6(SR)-5-hydroxy-6-(2-methylphenylthio)-6-phenyl-3-oxahexanoate is obtained in analogy to Example 14, stage 3, from butyl trans-5,6-epoxy-6-phenyl-3-oxahexanoate and 2-methylthiophenol.
$^1$H-NMR (60 MHz, CDCl$_3$, δ in ppm): 0.92 ("t", 3H), 1.0–1.7 (m, 4H), 2.37 (s, 3H), 2.95 (d br, 3 Hz, 1H), 3.4–3.8 (m, 2H), 4.08 (s)+3.9–4.4 (m) Σ6H, 7.0–7.5 (m, 9H).

EXAMPLE 17

Butyl 5(RS),6(SR)-5-hydroxy-6-(2-naphthylthio)-6-phenyl-3-oxahexanoate is obtained in analogy to Example 14, stage 3, from butyl trans-5-epoxy-6-phenyl-3-oxahexanoate and 2-mercaptonaphthalene.
Rf=0.14 (cyclohexane/ethyl acetate 4:1) $^1$H-NMR (60 MHz, CDCl$_3$, δ in ppm): 0.87 ("t", 3H), 1.2–1.8 (m, 4H), 2.93 (m, 1H), 3.4–3.8 (m, 2H), 3.98 (s, 2H) 4.0–4.5 (m, 4H), 7.0–7.8 (12H).

EXAMPLE 18

Butyl 5(RS),6(SR)-5-hydroxy-6-(4-fluorophenylthio)-6-phenyl-3-oxahexanoate is obtained in analogy to Example 1, stage 4, from butyl trans-5,6-epoxy-6-phenyl-3-oxahexanoate and 4-fluorothiophenol.
$^1$H-NMR (60 MHz, CDCl$_3$, δ in ppm): 0.89 ("t", 3H), 1.1–1.8 (m, 4H), 2.66 (s br, 1H), 3.4–3.8 (m, 2H), 4.02 (s, 2H), 4.0–4.3 (m, 4H), 6.77 (t, 9 Hz, 2H), 7.19 (t, 9 Hz)+7.19 (s) Σ7H.

EXAMPLE 19

Butyl 5(RS),6(SR)-5-hydroxy-6-(4-methoxyphenylthio)-6-phenyl-3-oxahexanoate is obtained in analogy to Example 1, stage 4, from butyl trans-5,6-epoxy-6-phenyl-3-oxahexanoate and 4-methoxythiophenol.

$^1$H-NMR (60 MHz, CDCl$_3$, δ in ppm): 0.92 ("t", 3H), 1.0–1.7 (m, 4H), 2.97 (m, 1H), 3.4–3.8 (m)+3.78 (s) Σ5H, 4.08 (s)+3.90–4.30 (m) Σ6H, 6.76 (d 9 Hz, 2H), 7.1–7.3 (m)+7.3 (s, br) Σ7H.

EXAMPLE 20

Butyl 5(RS),6(SR)-5-hydroxy-6-(2-methoxyphenylthio)-6-phenyl-3-oxahexanoate is obtained in analogy to Example 1, stage 4, from butyl trans-5,6-epoxy-6-phenyl-3-oxahexanoate and 2-methoxythiophenol.

$^1$H-NMR (60 MHz, CDCl$_3$, δ in ppm): 0.93 ("t", 3H), 1.0–1.8 (m, 4H), 3.30 (d, 3–4 Hz, 1H), 3.3–3.6 (m, 2H), 3.92 (s, 3H), 4.02 (s, 2H), 3.9–4.2 (m, 1H), 4.13 (t, 7 Hz, 2H), 4.41 (d, 5–6 Hz, 1H), 6.6–7.0 (m, 2H), 7.0–7.5 (m, 7H).

EXAMPLE 21

Butyl 5(RS),6(SR)-5-hydroxy-6-(3-methoxyphenylthio)-6-phenyl-3-oxahexanoate is obtained in analogy to Example 1, stage 4, from butyl trans-5,6-epoxy-6-phenyl-3-oxahexanoate and 3-methoxythiophenol.

$^1$H-NMR (60 MHz, CDCl$_3$, δ in ppm): 0.93 ("t", 3H), 1.0–1.8 (m, 4H), 2.97 (d, 4 Hz, 1H), 3.4–3.8 (m)+3.73 (s) Σ5H, 4.08 (s)+3.90–4.40 (m) Σ6H, 6.5–7.5 (m, 9H).

EXAMPLE 22

Heptyl 5(RS),6(SR)-5-hydroxy-6-(3-methoxyphenylthio)-6-phenyl-3-oxahexanoate

Stage 1: Heptyl (E)-6-phenyl-3-oxahex-5-enoate is obtained in analogy to Example 1, stage 2, by using n-heptanol in place of methanol as solvent.

$^1$H-NMR (60 MHz, CDCl$_3$, δ in ppm): 0.87 ("t", 3H), 1.0–1.8 (m, 10H), 4.08 (s, 2H), 4.10 (t, 6–7 Hz, 2H), 4.18 (d, 5 Hz, 2H), 5.9–6.7 (m, 2H), 7.0–7.4 (m, 5H).

Stage 2: Heptyl trans-5,6-epoxy-6-phenyl-3-oxahexanoate is obtained in analogy to Example 1, stage 3, from heptyl (E)-6-phenyl-3-oxahex-5-enoate.

$^1$H-NMR (60 MHz, CDCl$_3$, δ in ppm): 0.87 ("t", 3H), 1.1–1.8 (m, 10H), 3.1–3.4 (m, 1H), 3.6–4.0 (m, 3H), 4.10 (t, 6 Hz)+4.15 (s) Σ4H, 7.23 (s, 5H).

Stage 3: Heptyl 5(RS),6(SR)-5-hydroxy-6-(3-methoxyphenylthio)-6-phenyl-3-oxahexanoate is obtained in analogy to Example 1, stage 4, from heptyl trans-5,6-epoxy-6-phenyl-3-oxahexanoate and 3-methoxythiophenol.

Rf=0.13 (cyclohexane:ethyl acetate 4:1) $^1$H-NMR (60 MHz, CDCl$_3$, δ in ppm): 0.86 ("t", 3H), 1.0–1.6 (m, 10H), 2.70 (s, 1H), 3.4–3.8 (m)+3.66 (s) Σ5H, 4.00 (s)+3.90–4.40 (m) Σ6H, 6.5–7.3 (m, 9H).

EXAMPLE 23

Heptyl 5(RS),6(SR)-5-hydroxy-6-(4-methoxyphenylthio)-6-phenyl-3-oxahexanoate is obtained in analogy to Example 1, stage 4, from heptyl trans-5,6-epoxy-6-phenyl-3-oxahexanoate and 4-methoxythiophenol.

$^1$H-NMR (60 MHz, CDCl$_3$, δ in ppm): 0.86 ("t", 3H), 1.0–1.6 (m, 10H), 3.4–3.8 (m)+3.72 (s) Σ6H, 4.00 (s)+3.90–4.30 (m) Σ6H, 6.66 (d, 9 Hz)+7.20 (s) Σ7H.

EXAMPLE 24

Heptyl 5(RS),6(SR)-5-hydroxy-6-(2methoxyphenylthio)-6-phenyl-3-oxahexanoate is obtained in analogy to Example 1, stage 4, from heptyl trans-5,6-epoxy-6-phenyl-3-oxahexanoate and 2-methoxythiophenol.

$^1$H-NMR (60 MHz, CDCl$_3$, δ in ppm): 0.85 ("t", 3H), 1.0–1.6 (m, 10H), 3.15–3.3 (m, 1H), 3.3–3.6 (m, 2H), 3.85 (s, 3H), 3.96 (s, 2H), 3.9–4.2 (m, 3H), 4.32 (d, 5–6, 1H), 6.6–6.9 (m, 2H), 7.0–7.4 (m, 7H).

EXAMPLE 25

Hepthyl 5(RS),6(SR)-5-hydroxy-6-(2-aminophenylthio)-6-phenyl-3-oxahexanoate is obtained in analogy to Example 1, stage 4, from heptyl trans-5,6-epoxy-6-phenyl-3-oxahexanoate and 2-aminothiophenol.

$^1$H-NMR (60 MHz, CDCl$_3$, δ in ppm): 0.85 ("t", 3H), 1.0–1.8 (m, 10H), 3.4–3.6 (m, 2H), 3.93 (s, br)+4.00 (s)+3.80–4.30 (m) Σ11H, 6.3–7.3 (m)+7.20 (s) Σ9H.

EXAMPLE 26

Heptyl 5(RS),6(SR)-5-hydroxy-6-(3-aminophenylthio)-6-phenyl-3-oxahexanoate is obtained in analogy to Example 1, stage 4, from heptyl trans-5,6-epoxy-6-phenyl-3-oxahexanoate and 3-aminothiophenol.

$^1$H-NMR (60 MHz, CDCl$_3$, δ in ppm): 0.85 ("t", 3H), 1.0–1.8 (m, 10H), 3.2–3.6 (m, 5H), 3.98 (s)+3.9–4.4 (m) Σ7H, 6.3–7.3 (m)+7.20 (s, br) Σ9H.

EXAMPLE 27

Heptyl 5(RS),6(SR)-5-hydroxy-6-(2-methylphenylthio)-6-phenyl-3-oxahexanoate is obtained in analogy to Example 1, stage 4, from heptyl trans-5,6-epoxy-6-phenyl-3-oxahexanoate and 2-methylthiophenol.

$^1$H-NMR (60 MHz, CDCl$_3$, δ in ppm): 0.85 ("t", 3H), 1.0–1.8 (m, 10H), 2.32 (s, 3H), 2.93 (s, br, 1H), 3.4–3.8 (m, 2H), 4.00 (s, 2H), 4.1–4.3 (m, 4H), 6.8–7.4 (m)+7.23 (s) Σ9H.

EXAMPLE 28

Heptyl 5(RS),6-(SR)-5-hydroxy-6-(3-methylphenylthio)-6-phenyl-3-oxahexanoate is obtained in analogy to Example 1, stage 4, from heptyl trans-5,6-epoxy-6-phenyl-3-oxahexanoate and 3-methylthiophenol.

$^1$H-NMR (60 MHz, CDCl$_3$, δ in ppm): 0.85 ("t", 3H), 1.0–1.8 (m, 10H), 2.23 (s, 3H), 2.93 (d, br, 4 Hz, 1H), 3.4–3.8 (m, 2H), 3.98 (s, 2H), 3.9–4.4 (m, 4H), 6.8–7.4 (m)+7.23 (s) Σ9H.

EXAMPLE 29

Heptyl 5(RS),6(SR)-5-hydroxy-6-(4-fluorophenylthio)-6-phenyl-3-oxahexanoate is obtained in analogy to Example 1, stage 4, from heptyl trans-5,6-epoxy-6-phenyl-3-oxahexanoate and 4-fluorothiophenol.

$^1$H-NMR (60 MHz, CDCl$_3$, δ in ppm): 0.85 ("t", 3H), 1.0–1.8 (m, 10H), 2.97 (s, br, 1H), 3.4–3.8 (m, 2H), 4.00 (s, 2H), 4.0–4.2 (m, 5H), 6.75 (t, 9 Hz, 2H), 7.14 (t, 9 Hz)+7.15 (s) Σ7H.

EXAMPLE 30

Methyl 5(RS)6(SR)-5-hydroxy-6-(3-methoxyphenylthio)-6-phenyl-3-thiahexanoate.

Stage 1: trans-2,3-Epoxy-3-phenyl-1-propanol (racemic)

10 mmol (0.84 g) of NaHCO$_3$ are suspended in 30 ml of dry methylene chloride. While stirring, 10 mmol (2.8 g) of 3-chloroperbenzoic acid (85% pure) are added, and stirring is continued for 15 min; then 10 mmol (1.34 g) (E)-cinnamyl alcohol in 10 ml of methylene chloride are added dropwise. The mixture is then stirred at room temperature for 5 h, diluted with methylene chloride and washed with 2N sodium hydroxide solution and then 2× with water. The organic phase is dried over MgSO$_4$ and evaporated in vacuo. The residue is purified by medium pressure column chromatography on silica gel (35–70 μm) (eluent: cyclohexane/ethyl acetate 4:1). A pale oil is obtained.

Rf=0.14 (cyclohexane/ethyl acetate: 4:1) $^1$H-NMR (60 MHz, CDCl$_3$, δ in ppm): 1.8 (t, 1H), 3.20–3.25 (m, 1H), 3.72–3.85 (m, 1H), 4.03–4.10 (m, 1), 3.9 (d, 1H), 7.2–7.4 (m, 5)

Stage 2: trans-2,3-Epoxy-3-phenyl-1propyl p-toluene-sulfonate (racemic)

2.3 mmol (0.35 g) of stage 1 are dissolved in 20 ml of dry methylene chloride and, after addition of 0.75 ml of pyridine, the mixture is cooled to about 0° C. 2.4 mmol (0.46 g) of p-toluenesulfonyl chloride in 1 ml of methylene chloride are added, and the mixture is left to stir with exclusion of moisture in an ice bath for a further 6 h. It is diluted with 30 ml of ethyl acetate, and the organic phase is washed with water and dried over MgSO$_4$, and the solvent is removed by distillation in vacuo. Pale crystals, melting point 59° C. (from n-butanol)

Rf=0.54 (cyclohexane/ethyl acetate 2:1)

Stage 3: Methyl trans-5,6-epoxy-6-phenyl-3-thiahexanoate (racemic)

10 mmol (0.3 g) of NaH (80% in mineral oil) are suspended in 10 ml of n-hexane. 10 mmol (1 ml) of methyl thioglycolate are added dropwise to this, with exclusion of moisture, and the mixture is then stirred at room temperature for 1 h. The precipitated sodium salt is filtered off with suction, washed with n-hexane and dried under high vacuum.

2.3 mmol (0.65 g) of stage 2 are dissolved in 10 ml of dry tetrahydrofuran. To this is added in portions one half (about 5 mmol) of the sodium salt described above, and the mixture is then stirred under a nitrogen atmosphere at room temperature for 2 h. It is then diluted with methylene chloride, the precipitated salts are removed by filtration, and the filtrate is concentrated in vacuo. A pale yellow oil is obtained.

Rf=0.61 (cyclohexane/ethyl acetate 2:1) $^1$H-NMR (60 MHz, CDCl$_3$, δ in ppm): 2.8–3.0 (AB-m, 2H), 3.1–3.4 (m, 1H), 3.4 (s, 2H), 3.6–3.9 (m, 1H), 3.7 (s, 3H), 7.1–7.5 (m, 5H).

Stage 4: Methyl 5(RS),6(SR)-5-hydroxy-6-(3-methoxyphenylthio)-6-phenyl-3-thiahexanoate 1.2 mmol (0.28 g) of stage 3 are dissolved in 5 ml of dry tetrahydrofuran, and 1.5 mmol (0.21 g) of 3-methoxythiophenol and 0.3 ml of triethylamine are added. The reaction mixture is stirred under a nitrogen atmosphere at 40° C. for 24 h, and is then concentrated. The residue is dissolved in ethyl acetate, and the solution is washed with saturated NaCl solution, dried over MgSO$_4$ and concentrated in vacuo. The product is purified by medium pressure column chromatography on silica gel (35–70 μm) (eluent cyclohexane/ethyl acetate 4:1). A pale oil is obtained.

Rf=0.21 (cyclohexane/ethyl acetate 4:1)

$^1$H-NMR (60 MHz, CDCl$_3$, δ in ppm): 1.3 (s, br, 1H), 2.7–2.95 (AB-m, 2), 3.3 (s, 2H), 3.6–3.9 (m, 1H), 3.7 (s, 3H), 7.1–7.5 (m, 5H).

EXAMPLE 31

Methyl (5R,6S)-(+)-5-hydroxy-6-(3-methoxyphenylthio)-6-phenyl-3-thiahexanoate

Stage 1: (2R,3R)-(+)-2,3-Epoxy-3-phenyl-1-propanol 4 g of 4 Å molecular sieves are suspended in 200 ml of dry methylene chloride. The suspension is cooled to −5° C. and, while stirring, 7.5 mmol (1.6 g) of diethyl D-(−)-tartrate and 5.0 mmol (1.5 g) of titanium(IV) isopropylate are successively added, and the mixture is then cooled to −25° C. Then 150 mmol (50 ml of 3-molar solution in toluene) of t-butyl hydroperoxide are added, and the mixture is stirred for a further 10 min. Subsequently 100 mmol (13.4 g) of trans-cinnamyl alcohol in 50 ml of methylene chloride are added within 10′. The mixture is stirred at −10° C. for 8 h, then 30 ml of water are added, and the mixture is warmed to room temperature. To hydrolyse the tartrates, 7 ml of a solution of 10 g of NaCl and 30 g of NaOH in 80 ml are added dropwise. The organic phase is separated off, and the aqueous phase is extracted 2× with methylene chloride. The combined organic phases are dried over MgSO$_4$, filtered and evaporated in vacuo. The crude product is purified by column chromatography on silica gel (eluent cyclohexane/etyhyl acetate 4:1).

White crystals, melting point 49° C.
Rf=0.31 (cyclohexane/ethyl acetate 2:1)
$[\alpha]^D$ = +49° (c=2, CHCl$_3$)
−H NMR identical to Example 30, stage 1.

Stages 2 to 4 are carried out in analogy to Example 30. The spectroscopic data of the products are identical to those of the racemic compounds from Example 30.

(2R,3R)-(+)-2,3-Epoxy-3-phenyl-1-propyl-p-toluenesulfonate Melting point: 56° C. $[\alpha]^D$ = +75.2° (c=1, CHCl$_3$)

Methyl (5R,6R)-(+)-5,6-Epoxy-6-phenyl-3-thiahexanoate $[\alpha]^D$ = +45° (c=2, CHCl$_3$)

Methyl (5R,6R)-(+)-5-Hydroxy-6-(3-methoxyphenylthio)-6-phenyl-3-thiahexanoate $[\alpha]^D$ = +133.6° (c=2, CH$_3$OH)

The optical purity was determined by $^1$H-NMR spectroscopy in the presence of an optically active europium shift reagent (Eu(tfc)$_3$=europium(III)-[3-(trifluormethylhydroxymethylene)-d-camphorate], 5 mg of Example 31+25 mg of Eu(tfc)$_3$ in 0.5 ml of CDCl$_3$) by integration of the methyl ester signals to be >99%.

EXAMPLE 32

Methyl (5R,6R)-(−)-5-hydroxy-6-(3-methoxyphenylthio)-6-phenyl-3-thiahexanoate (2S,3S)-(−)-2,3-Epoxy-3-phenyl-1-propanol is prepared in analogy to Example 31, stage 1, by use of diethyl L-(+)-tartrate. $[\alpha]^D$ = −49° (c=2, CHCl$_3$)).

Stages 2 to 4 are carried out in analogy to Example 30. The spectroscopic data of the products are identical to those of the racemic compounds from Example 30.

(2S,3S)-(−)-2,3-Epoxy-3-phenyl-1-propyl p-toluenesulfonate

Melting point: 56° C.
$[\alpha]^D$ = −75.2° (c=1, CHCl$_3$)
Methyl (5S,6S)-(−)-5,6-Epoxy-6-phenyl-3-thiahexanoate $[\alpha]^D$ = −45 (c+2, CHCl$_3$)

Methyl (5S,6R)-(−)-5-hydroxy-6-(3-methoxyphenyl-thio)-6-phenyl-3-thiahexanoate $[\alpha]^D = -133.6°$ (c=2, $CH_3OH$)

The optical purity was determined by $^1$H-NMR spectroscopy in the presence of an optically active europium shift reagent (Eu(tfc)$_3$=europium(III)-[3-(trifluoromethylhydroxymethylene)-d-camphorate], 5 mg of Example 32+25 mg of Eu(tfc)$_3$ in 0.5 ml of CDCl$_3$ by integration of the methyl ester signals to be >99%.

EXAMPLE 33

Dimethyl (5RS,6RS)-5-hydroxy-6-phenyl-3,7-dithiadecanedioate is obtained in analogy to Example 14 from methyl trans-5,6-epoxy-6-phenyl-3-thiahexanoate (Example 30, stage 3) and methyl 3-mercaptopropionate.

Pale oil, Rf=0.39 (cyclohexane/ethyl acetate 1:1)
$^1$H-NMR (60 MHz, CDCl$_3$, δ in ppm): 2.4–2.7 (m, 4H), 2.7–2.9 (m, 3H), 3.28 (s, 2H), 3.63 (s 3H), 3.70 (s, 3H), 4.0 (m, 2H), 7.29 (s, br, 5H)

EXAMPLE 34

(5RS,6SR)-5-Hydroxy-6-(2-aminophenylthio)-6-phenyl-3-oxahexanamide

Stage 1: (E)-6-phenyl-3-oxahex-5-enamide 26 mmol (5.0 g) of (E)-6-phenyl-3-oxahex-5-enoic acid (Example 1, stage 1) are dissolved in 60 ml of dry tetrahydrofuran. While cooling in an ice bath, 4.65 g of of carbonyldiimidazole are added, stirring in the ice bath is continued for 30 min, and the mixture is then cooled to −40° C., 20 ml of liquid ammonia are added dropwise, and the mixture is stirred at −40° C. for 30 min and then allowed slowly to reach room temperature and is stirred further overnight. The solvent is evaporated off, the residue is taken up in ethyl acetate, and the solution is washed with water, dried over Na$_2$SO$_4$ and concentrated. The residue is recrystallized from diisopropyl ether/methanol (10:1).

White solid, melting point 125°6° C. Rf=0.65 (cyclohexane/ethyl acetate 1:1)
$^1$H-NMR (60 MHz, CDCl$_3$, δ in ppm): 3.83 (s, 2H), 4.12 (d, 5 Hz, 2H), 6.0–6.8 (m, 2H), 6.9–7.5 (m, 7H).

Stage 2: trans-5,6-Epoxy-6-phenyl-3-oxahexanamide is obtained in analogy to Example 1 from the compound described above. Crystallizes from diisopropyl ether/ethyl acetate 20:1

White solid, melting point 93°94° C. Rf=0.56 (CHCl$_3$/CH$_3$OH 4:1)
$^1$H-NMR (60 MHz, CDCl$_3$ δ in ppm): 3.1–3.3 (m, 1H), 3.4–3.9 (m, 3H), 4.0 (s, 2H), 5.9–6.9 (m, br, 2H), 7.23 (s, 5H).

Stage 3:
(5RS,6SR)-5-Hydroxy-6-(3-aminophenylthio)-6-phenyl-3-oxahexanamide is obtained from stage 2 and 2-aminophenol in analogy to Example 1.

Solid, melting point 111°–112° C.
Rf=0.3 (CHCl$_3$/CH$_3$OH 8:1)
$^1$H-NMR (60 MHz, CDCl$_3$, δ in ppm): 2.33 (s, br, 1H), 3.48 (m, 2H), 3.76 (s, 2H), 3.9–4.4 (m, 5H), 6.3–7.2 (m, 4H), 7.18 (s, 5H).

EXAMPLE 35

Sodium (5RS,6RS)-5-Hydroxy-6-(2-naphthylthio)-6-phenyl-3-oax-hexanoate 2 mmol of methyl (5RS,6SR)-5-hydroxy-6-(2-naphthylthio)-6-phenyl-3-oxahexanoate (Example 2) are dissolved in 10 ml of tetrahydrofuran. 1 ml of 2N sodium hydroxide solution is added, the mixture is stirred at room temperature for 4 h, and the resulting precipitate is filtered off and dried in vacuo. White solid, melting point 208°–210° C.
$^1$H-NMR (60 MHz, DMSO-d$_6$, δ in ppm): 3.0–3.8 (m)+3.33 (s, br)+3.55 (s, br) Σ5H, 3.9–4.2 (m, 1H), 4.53 (d, 6 Hz, 1H), 7.0–7.8 (m, 12H).

EXAMPLE 36

Dimethyl (5RS),(6SR)-5-hydroxy-6-[2-(1-E-dodecenyl]-3,7-dithiadecanedioate

Stage 1: 2-(1-E-dodecenyl)benzaldehyde 0.5 mol (92.5 g) of 2-bromobenzaldehyde are dissolved in 600 ml of DMF. To this solution are added 1.5 mol (207 g) of powdered potassium carbonate, 0.55 mol (92.6 g) of 1-dodecene, 0.2 mol (64.4 g) of tetrabutylammonium bromide and 2.5 g of palladium(II) acetate. The mixture is stirred under a nitrogen atmosphere at 50° C. for 6 h. The mixture is filtered, the residue is washed with a little DMF, and the filtrate is diluted with 2–3 liters of water. It is extracted 3–4× with n-hexane, and the extracts are washed with water (3×) and saturated brine (1×), dried over Na$_2$SO$_4$ and concentrated in vacuo. The dark residue is purified by column chromatography on silica gel (70–200 μm, eluent cyclohexane:ethyl acetate 19:1). The GC integration indicates that the product contains about 30% of 2-(2-dodecenyl)benzaldehyde.

Rf=0.72 (cyclohexane/ethyl acetate 9:1)
$^1$H-NMR (60 MHz, CDCl$_3$, δ in ppm): 0.87 (t, br, 5 Hz, 3H), 1.1–1.7, 1.8–2.4 (m, Σ18H), 6.1 (dt, Jd=16 Hz, Jt=6–7 Hz, 1H), 7.0–7.8 (m, 5H), 10.3 (s, 1H).

Stage 2: (E,E)-3-[2-(1-dodecenyl)phenyl]propenoic acid 40 ml of 50% strength sodium hydroxide solution are mixed with 60 ml of toluene. 0.3 g of tetrabutylammonium bromide is added and then, while stirring vigorously, a solution of 36.7 mmol (10 g) of stage 1 and 50 mmol (10 ml) of triethyl phosphonoacetate in 20 ml of toluene is added dropwise, during which the internal temperature should be 20°–40° C. The mixture is then stirred for 90 minutes, diluted with 200 ml of ethanol and stirred at room temperature for a further 3 h. Most of the ethanol is removed by distillation in vacuo, and the residue is acidified with concentrated hydrochloric acid and extracted several times with ethyl acetate. The combined extracts are washed with water and saturated brine, dried over Na$_2$SO$_4$ and evaporated in vacuo. The residue is recrystallized from n-hexane (2–3×). While solid, melting point 85°–6° C.
$^1$H-NMR (270 MHz, CDCl$_3$, δ in ppm): 0.88 (t, 6.5 Hz, 3H), 1.2–1.6 (m, 18H), 2.27 (q, 7 Hz, 2H) 6.09 (dt, 16 Hz, 1H), 6.37 (d, 16 Hz) 6.69 (d, 16 Hz, 1H), 7.25 (td, 7–8 Hz, 0–1 Hz, 1H), 7.34 (td, 7–8 Hz, 0–1 Hz, 1H), 7.44 (dd, 8 Hz, 0–1 Hz, 1H), 7.56 (dd, 8 Hz, 0–1 Hz, 1H), 8.18 (d, 16 Hz, 1H).

Stage 3: Methy (E,E)-3-[2-(1-dodecenyl)phenyl]propenoate 15 mmol (4.7 g) of stage 2 are stirred in 100 ml of dry acetone with 15 g of powdered K$_2$CO$_3$ and 30 mmol (2.85 ml) of dimethyl sulfate under a nitrogen atmosphere at 40° C. for 4 h. The mixture is poured into 300 ml of dilute ammonia solution (diluted 1:10), and the mixture is stirred for 5 min and then extracted several times with n-hexane. The extract are washed with water, dried over Na₂SO₄ and concentrated vacuo. The residue can be used directly for further reaction.

¹H-NMR (270 MHz, CDCl₃, δ in ppm): 0.88 (t, 6.5 Hz, 3H), 1.2–1.6 (m, 18H), 2.26 (qd, 8 Hz, 1 Hz, 2H), 3.81 (s, 3H), 6.08 (dt, 16 Hz, 8 Hz, 1H), 6.34 (d, 16 Hz, 1H), 6.69 (d, 16 Hz, 1H), 7.22 (td, 7–8 Hz, 1–2 Hz, 1H), 7.32 (td, 7–8 Hz, 1–2 Hz, 1H), 7.43 (dd, 8 Hz, 1–2 Hz, 1H), 7.51 (dd, 8 Hz, 1–2 Hz, 1H), 8.06 (d, 16 Hz, 1H).

Stage 4: (E,E)-3-[2-(1-dodecenyl)phenyl]prop-2-en-1-ol 14.4 mmol of diisobutylaluminum hydride (12 ml of 1.2 molar solution in toluene) are diluted with a further 10 ml of toluene. To this is added dropwise, under a nitrogen atmosphere and while cooling in an ice bath, 5.78 mmol (1.9 g) of stage 3 dissolved in 10 ml of toluene. The mixture is left to stir for 1 h and then, to decompose the excess hydride, 1 ml of ethyl acetate is added dropwise, and the mixture is left to stir for 10 min and then cautiously poured into 100 ml of dilute sulfuric acid (1–2 normal). The organic phase is separated off, and the aqueous phase is extracted with ether. The combined organic phases are washed with water, saturated NaHCO₃ and NaCl solutions, dried over Na₂SO₄ and concentrated in vacuo. The residue is purified by column chromatography on silica gel (70–200 μm, eluent ethyl acetate/cyclohexane 1:19→1:9). The product solidifies to a wax-like white mass without a sharp melting point.

Rf=0.3 (CH₂Cl₂) ¹H-NMR (270 MHz, CDCl₃, δ in ppm): 0.87 (t, 6.5 Hz, 3H), 1.2–1.6 (m, 19H), 2.24 (q or dt, 7.5 Hz, 2H), 4.35 (d, 6Hz, 2H), 6.06 (dt, 15.5 Hz, 7.5 Hz, 1H), 6.23 (dt, 15.5 Hz, 6 Hz, 1H), 6.64 (d, 15.5 Hz, 1H), 6.91 , (d, 15.5 Hz, 1H), 7.20 (m, 2H), 7.4 (m, 2H).

Stage 5: (2RS,3RS)-3-[2-(1-(E)-dodecenyl)phenyl]-2,3-epoxypropanol 7.6 mmol (2.28 g) of stage 4 stage 4 are dissolved in 50 ml of dry methylene chloride. 11.4 mmol of t-butyl hydroperoxide (11.4 ml, 1 M in toluene) and 40 mg of vanadyl acetylacetonate are added, and the mixture is stirred under a nitrogen atmosphere at room temperature overnight. The solution is washed with NaHCO₃ solution and water, dried over Na₂SO₄ and evaporated in vacuo. The crude product is reacted further without purification.

Stage 6: Methyl (5RS),(6SR)-6,7-dihydroxy-5-[2-(1-E-dodecenyl)-phenyl]-4-thiaheptanoate 3.8 mmol (1.2 g) of stage 5 and 2 ml (about 5 eq.) of methyl 3-mercaptopropionate are dissolved in 10 ml of methanol. 0.5 ml of triethylamine is added, and the mixture is left to stand under a nitrogen atmosphere at room temperature for 3 days. The solution is then diluted with t-butyl methyl ether, washed with 2N H₂SO₄, water and saturated NaCl solution, dried over Na₂SO₄ and evaporated in vacuo. The residue is purified by medium pressure column chromatography on silica gel (35–70 μm, eluent t-butyl methyl ether/cyclohexane 1:3). A pale oil is obtained.

Rf=0.65 (t-butyl methyl ether) ¹H-NMR (270 MHz, CDCl₃, δ in ppm): 0.89 (t, 6.5 Hz, 3H), 1.2–1.35 (m, 14H), 1.47 (q, 6–7 Hz, 2H), 2.07 (m, 1–2H), 2.24 (q, 7 Hz, 2H), 2.48 (m, 2H), 2.61–2.71 (m, 2H), 3.66 (s, 3H), 3.7–3.85 (m 1H), 4.41 (d, 8 Hz, 2H), 6.05 (dt, 16 Hz, 7 Hz, 1H), 6.73 (d, 16 Hz, 1H), 7.18–7.3 (m, 2H), 7.38 (dd, 7 Hz, 1H), 7.52 (d, br, 7 Hz, 1H).

Stage 7: Methyl (5RS,(6SR)-5-[2-(1-E-dodecenyl)phenyl]-6-hydroxy-7-(4-toluenesulfonyloxy)-4-thiaheptanoate 1.15 mmol (0.5 g) of stage 6 are dissolved in 1 ml of absolute pyridine. The solution is cooled in an ice bath to 0°–5° C., with exclusion of moisture, and then 1.25 mmol (0.24 g) of p-toluenesulfonyl chloride are added. The mixture is left to stir in the ice bath for a further 30 min and then at room temperature for 3 h, and is then diluted with t-butyl methyl ether and water, the phases are separated, and the organic phase is washed with 2N H₂SO₄, water and saturated NaHCO₃ solution. After drying over Na₂SO₄, the solvent is evaporated off in vacuo. The crude product is reacted without further purification.

¹H-NMR (60 MHz, CDCl₃, δ in ppm): 0.88 ("t", br), 1.1–1.9 (m), 1.9–2.8 (m), 2.45 (s), 3.66 (s), 3.2–4.5 (m), 6.0–6.8 (m), 7.0–7.6 (m), 7.8 (d, 8–9 Hz)

Stage 8: Dimethyl (5RS),(6SR)-5-hydroxy-6-[2-(1-E-dodecenyl)phenyl]-3,7-dithiadecanedioate 5 mmol (115 mg) of sodium are dissolved in 10 ml of dry methanol under a nitrogen atmosphere. 6 mmol (640 mg) of methyl thioglycolate, and then 1 mmol (590 mg) of stage 7, are added, and the mixture is stirred at 40° C. for 6 h. The solution is poured into 2N sulfuric acid, the mixture is extracted 3× with ethyl acetate, the organic phase is washed with water, NaHCO₃ and NaCl solutions and dried over Na₂SO₄, and the solvent is removed by distillation in vacuo. The residue is purified by column chromatography on silica gel (35–70 μm, eluent cyclohexane/ethyl acetate 9:1→4:1).

¹H-NMR (270 MHz, CDCl₃, δ in ppm): 0.89 (t, 6.5 Hz, 3H), 1.2–1.35 (m, 14H), 1.47 (q, 6–7 Hz, 2H), 2.07 (m, 1–2H), 2.24 (q, 7 Hz, 2H), 2.48 (m, 2H), 2.61–2.71 (m, 2H), 3.29 (s, br, 2H), 3.63 (s, 3H), 3.67 (s, 3H), 3.7–3.85 (m, 1H), 4.41 (d, 8 Hz, 1H), 6.08 (dt, 16 Hz, 7 Hz, 1H), 6.71 (d, 16 Hz, 1H), 7.18–7.3 (m, 2H), 7.38 (dd, 7 Hz, 3 Hz, 1H), 7.52 (d, br, 7 Hz, 1H).

EXAMPLE 37

Dimethyl (5RS),(6SR)-6-[2-benzyloxy-3-cyclopentylphenyl]-5-hydroxy-3,7-dithiadecanedioate Stage 1: 3-Cyclopentyl-2-hydroxybenzaldehyde 1 mol (162 g) of 2-cyclopentylphenol is dissolved in 200 ml of dry toluene. While stirring vigorously and with exclusion of moisture, 0.1 mol (26 g) of tin tetrachloride and 0.45 mol (159.3 g) of trioctylamine are successively added dropwise and, after being left to stir at room temperature for 20 min., 2.2 mol (66 g) of paraformaldehyde are added to the resulting suspension. It is subsequently heated at 100° C. for 6–8 h, then poured into 4 liters of ice-water, and the pH is adjusted to 1–2 with 2N hydrochloric acid. The mixture is extracted several times with ethyl acetate, and the combined extracts are washed with saturated NaCl solution, dried over Na₂SO₄ and concentrated in vacuo. The crude product is purified by column chromatography on silica gel (70–200 μm, eluent cyclohexane). An oil is obtained. Rf=0.62 (CH₂Cl₂)

¹H-NMR (60 MHz, CDCl₃, δ in ppm): 1.2–2.4 (m, 8HO, 3.0–3.6 (m, 1H), 6.8–7.2 (m, 3H), 9.9 (s, 1H), 11.4 (s, 1H).

Stage 2: 2-Benzyloxy-3-cyclopentylbenzaldehyde 0.19 mol (36.2 g) of stage 2 is dissolved in 100 ml of dimethylformamide. 0.95 mol (131 g) of $K_2CO_3$ (powdered) and 0.228 mol (28.9 g) of benzyl chloride are added, and the mixture is stirred with exclusion of moisture at 30° C. for 4 h. It is diluted with 1 liter of ice-water and extracted several times with t-butyl methyl ether, the combined extracts are washed with water and brine and dried over $Na_2SO_4$, and the solvent is removed by distillation in vacuo. The crude product is purified by column chromatography on silica gel (70–200 μm, eluent cyclohexane). A clear oil is obtained.

$^1$H-NMR (60 MHz, CDCl$_3$, δ in ppm): 1.4–2.2 (m, 8H), 3.2–3.6 (m, 1H), 4.95 (s, 2H), 7.0–7.8 (m), and 7.4 (s), Σ8H, 10.25 (s, 1H).

Stage 3:

(E)-3-(2-benzyloxy-3-cyclopentylphenyl)propenoic acid is obtained from stage 2 in analogy to Example 36, stage 2.

White crystals, melting point 115°–116° C.

$^1$H-NMR (60 MHz, CDCl$_3$, δ in ppm): 1.3–2.2 (m, 8H), 3.2–3.7 (m, 1H), 4.8 (s, 2H), 6.39 (d, 16 Hz, 1H), 7.0–7.6 (m) and 7.4 (s) Σ8H, 8.10 (d, 16 Hz, 1H), 10.6 (s, br, 1H).

Stage 4:

(E)-3-(2-benzyloxy-3-cyclopentylphenyl)propenoate is obtained from stage 3 in analogy to Example 36, stage 3 (oil).

$^1$H-NMR (60 MHz, CDCl$_3$, δ in ppm): 1.3–2.2 (m, 8H), 3.2–3.7 (m, 1H), 3.8 (s, 3H), 4.83 (s, 2H), 6.46 (d, 16 Hz, 1H), 7.0–7.6 (m) and 7.45 (s), Σ8H, 8.10 (d, 16 Hz, 1H).

Stage 5:

(E)-3-(2-benzyloxy-3-cyclopentylphenyl)prop-2-en-1-ol is obtained from stage 4 in analogy to Example 36, stage 4 (oil).

$^1$H-NMR (60 MHz, CDCl$_3$, δ in ppm): 1.2–2.2 (m, 8–9H), 3.2–3.7 (m, 1H), 4.22 (d, 6Hz, 2H), 4.8 (s, 2H), 6.26 (dt, 16Hz, 6Hz, 1H), 6.87 (d, 16Hz, 1H), 7.0–7.5 (m) and 7.37 (s), Σ 8H.

Stage 6:

(2RS,3RS)-3-(2-Benzyloxy-3-cyclopentylphenyl)-2,3-epoxypropanol is obtained from stage 5 in analogy to Example 36, stage 5 (oil).

$^1$H-NMR (270 MHz, CDCl$_3$, δ in ppm): 1.4–1.85 (m, 6H), 1.9–2.15 (m, 2H), 3.163 (ddd, 1H), 3.3–3.5 (m, 2H), 4.681 (dd, 14Hz, 4Hz, 1H), 4.921 (dd, 14Hz, 3Hz, 1H), 4.215 (d, 3Hz, 1H), 4.907, 4.929 (AB, 10Hz, 2H), 7.0–7.6 (m, 8H).

Stage 7: Methyl (5RS), (6SR)-5-(2-benzyloxy-3-cyclopentylphenyl)-6,7-dihydroxy-4-thiaheptanoate is obtained from stage 6 in analogy to Example 36, stage 6 (oil).

$^1$H-NMR (60 MHz, CDCl$_3$, δ in ppm): 1.4–2.2 (m, 8–9H), 2.27 (m, 2H), 2.4–3.0 (m, 4H), 3.2–4.2 (m)+3.60 (s) Σ 6H, 4.46 (d, 7Hz, 1H), 4.78 and 5.00 (AB, 11Hz 2H), 7.0–7.5 (m, 8H).

Stage 8: Methyl (5RS),(6SR)-5-(2-benzyloxy-3-cyclopentylphenyl)-6-hydroxy-7-(4-methanesulfonyloxy)-4-thiaheptanoate 10 mmol of stage 7 are dissolved in 20 ml of dry methylene chloride. 15 mml of triethylamine are added, and the mixture is cooled under a nitrogen atmosphere to −10° to −20° C. and 10.5 mmol of methanesulfonyl chloride dissolved in a little methylene chloride are added dropwise. The mixture is left to stir in a cooling bath for a further 30 min, diluted with t-butyl methyl ether and washed with 2N hydrochloric acid, water and saturated brine, dried over $Na_2SO_4$ and concentrated in vacuo. The crude product is reacted further without purification.

$^1$H-NMR (60 MHz, CDCl$_3$, δ in ppm): 1.4–2.2 (m, 8–9H), 2.4–3.0 (m)+2.94 (s) Σ 7–8H, 3.2–4.0 (m)+3.67 (s) Σ5H, 4.0–4.6 (m, 3H), 4.94 (s, br, 2H), 7.0–7.5 (m, 8H).

Stage 9: Dimethyl (5RS),(6SR)-5-hydroxy-6-(2-benxyloxy-3-cyclopentylphenyl)-3,7-dithiadecanedioate is obtained from stage 8 in analogy to Example 36, stage 8 (oil).

$^1$H-NMR (270 MHz, CDCl$_3$, δ in ppm): 1.5–1.75 (m, 4H), 1.75–1.9 (m, 2H), 2.0–2.15 (m, 2H), 2.485 (t, 7Hz, 2H), 2.6–2.7 (m, 2H), 2.742 (dd, 14Hz, 8Hz, 1H), 3.052 (dd, 14Hz, 3–4Hz, 1H), 3.291, 3.322 (AB, 14Hz, 2H), 3.35–3.45 (m, 1–2H), 3.633 (s, 3H), 4.141 (td, 8Hz, 3–4Hz, 1H), 4.533 (d, 8Hz, 1H), 4.866 (d, 12Hz, 1H), 4.999 (d, 12Hz, 1H), 7.148 (t, 8Hz, 1H), 7.238 (dd, 8Hz, 1–2Hz, 1H), 7.3–7.55 (m, 6H).

EXAMPLE 38

Dimethyl (RS),(6SR)-6-[2-(4-methoxybenzyloxy)-3-cyclopentylphenyl]-5-hydroxy-3,7-dithiadecanedioate $^1$H-NMR (270 MHz, CDCl$_3$, δ in ppm): 1.5–1.75 (m, 4H), 1.75–1.9 (m, 2H), 2.0–2.15 (m, 2H), 2.485 (t, 7Hz, 2H), 2.6–2.7 (m, 2H), 2.756 (dd, 15Hz, 8Hz, 1H), 3.046 (dd, 15Hz, 3–4Hz, 1H), 3.326 (s, 2H), 3.45–3.5 (m, 1H), 3.629 (s, 3H), 3.685 (s, 3H), 3.844 (s, 3H), 4.1–4.2 (m, 1H), 4.534 (d, 8Hz, 1H), 4.790 (d, 12Hz, 1H), 4.923 (d, 12Hz, 1H), 6.947 (d, 8Hz, 2H), 7.142 (t, 8Hz, 1H), 7.233 (dd, 8Hz, 1–2Hz, 1H), 7.354 (dd, 8Hz, 1–2Hz, 1H), 7.432 (d, 8Hz, 1H). is obtained in analogy to Example 37 via the following intermediates:

2- (4-Methoxybenzyloxy)-3-cyclopentylbenzaldehyde (from Example 37, stage 1, and 4-methoxybenzyl chloride)

$^1$H-NMR (60 MHz, CDCl$_3$, δ in ppm): 1.4–2.2 (m, 8H), 3.2–3.6 (m, 1H), 3.77 (s, 3H), 4.85 (s, 2H), 6.7–7.7 (m, 7H), 10.22 (s, 1H).

Ethyl (E)-3-[2-(4-methoxybenzyloxy)-3-cyclopentylphenyl]-propenoate 10 mmol (3.1 g) of 2-(4-methoxybenzyloxy)-3-cyclopentylbenzaldehyde are heated with 10 mmol (2 ml) of triethyl phosphonoacetate, 6.9 g of $K_2CO_3$ (powdered) and 0.5 g of $Bu_4NBr$ in 25 ml of toluene at 100° C. while stirring and excluding moisture for 4 h. After 2 h, an additional 0.5 ml of triethyl phosphonoacetate is added. The mixture is allowed to cool and is filtered, diluted with ethyl acetate, washed with 2N $H_2SO_4$, water and brine, dried over $Na_2SO_4$ and concentrated in vacuo. The crude product is purified by column chromatography on silica gel (70–200 μm, eluent $CH_2Cl_2$/n-hexane 1:1). Oil.

$^1$H-NMR (60 MHz, CDCl$_3$, δ in ppm):
1.30 (t, 7Hz, 3H), 1.4–2.2 (m, 8H), 3.2–3.6 (m, 1H), 3.80 (s, 3H), 4.20 (q, 7Hz, 2H), 4.70 (s, 2H), 6.36 (d, 16Hz, 1H), 6.7–7.7 (m), 6.85 (d, 9Hz), 7.30 (d, 9Hz) Σ 7H, 8.0 (d, 16Hz, 1H).

(E) -3-[2- (4-Methoxybenzyloxy)-3-cyclopentylphenyl]-prop-2-en-1-ol

¹H-NMR (60 MHz, CDCl₃, β in ppm): 1.2–2.2 (m, 8–9H), 3.2–3.7 (m, 1H), 3.78 (s, 3H), 4.22 (d, 5.5–6Hz, 2H), 4.7 (s, 2H), 6.28 (dt, 16Hz, 5.5–6Hz, 1H), 6.7–7.5 (m, 8H).

(2RS,3RS)-3-[2-(4-Methoxybenzyloxy)-3-cyclopentylphenyl]-2,3-epoxypropanol

¹H-NMR (270 MHz, CDCl₃δ in ppm): 1.5–1.9 (3m, Σ 7H), 1.95–2.10 (m, 2H), 3.160 (m, 1H), 3.441 (m, 1H), 3.55–3.60 (m, 1H), 3.829 (s, 3H), 3.9–4.0 (m, 1H), 4.225 (d, 3Hz, 1H), 4.824 (s, 2H), 6.935 (d, 8Hz, 2H), 7.023 (dd, 8Hz, 1–2Hz, 1H), 7.111 (t, 8Hz, 1H), 7.253 (dd, 8Hz, 1–2Hz, 1H), 7.371 (d, 8Hz, 1H).

Methyl (5RS),(6SR)-5-[2-(4-methoxybenzyloxy)-3-cyclopentylphenyl]-6,7-dihydroxy-4-thiaheptanoate ¹H-NMR (270 MHz, CDCl₃, δ in ppm): 1.5–1.9 (m, 6H), 2.0–2.15 (m, 2H), 2.355 (s, br, 2H), 2.525 (t, 7Hz, 2H), 2.687 (t, 7Hz, 2H), 2.687 (t, 7Hz, 2H), 3.45–3.5 (m, 1H), 3.654 (s+m, 5H), 3.842 (s, 3H), 4.0–4.1 (m, 1H), 4.536 (d, 8Hz, 1H), 4.775 (d, 12Hz, 1H), 4.909 (d, 12Hz, 1H), 6.952 (d, 8Hz, 2H), 7.158 (t, 8Hz, 1H), 7.252 (dd, 8Hz, 1–2Hz, 1H), 7.333 (dd, 8Hz, 1H), 7.419 (d, 8Hz, 1H).

Methyl (5RS),(6SR)-5-[2-(4-methoxybenzyloxy)-3-cyclopentylphenyl]-6-hydroxy-7-methanesulfonyloxy-4-thiaheptanoate ¹H-NMR (60 MHz, CDCl₃, δ in ppm): 2.97 (s, 3H), 3.67 (s, 3H), 3.84 (s, 3H), 4.87 (s, br, 1H)

EXAMPLE 39

Dimethyl (5RS),(6SR)-6-[2-(2-phenylethoxy)-3-cyclopentylphenyl]-5-hydroxy-3,7-dithiadecanedioate ¹H-NMR (270 MHz, CDCl₃, δ in ppm): 1.4–1.65 (m, 4H), 1.65–1.8 (m, 2H), 1.85–2.0 (m, 2H), 2.4–2.65 (m, 5H), 3.959 (dd, 14Hz, 3–4Hz, 1H), 3.107 (t, 6Hz)+3.0–3.15 (m) Σ 3–4H), 3.333 (s, 7H), 3.666 (s, 3H), 3.718 (s, 3H), 3.9–4.1 (m, 3H), 4.206 (d, 8Hz, 1H), 7.0–7.4 (m, 8H) is obtained in analogy to Example 37 via the following intermediates:

2-(2-Phenylethoxy)-3-cyclopentylbenzaldehyde (from Example 37, stage 1 and 2-phenylethyl bromide)

¹H-NMR (60 MHz, CDCl₃, δ in ppm): 1.4–2.2 (m, 8H), 3.1 (t, 7Hz, 2H), 3.2–3.6 (m, 1H), 4.06 (t, 7Hz, 2H), 7.26 (s)+6.7–7.7 (m) Σ 8H, 10.15 (s, 1H).

Ethyl (E)-3-[2-(2-phenylethoxy)-3-cyclopentylphenyl]-propenoate (prepared in analogy to Example 38 )

¹H-NMR (60 MHz, CDCl₃, δ in ppm): 1.30 (t, 7Hz, 3H), 1.4–2.2 (m, 8H), 3.1 (t, 7Hz, 2H), 3.2–3.6 (m, 1H), 3.98 (t, 7Hz, 2H), 4.22 (q, 7Hz, 2H), 6.36 (d, 16Hz, 1H), 7.21 (s), 6.7–7.7 (m) Σ 8H, 7.95 (d, 16Hz, 1H).

(E)-3-[2-Phenylethoxy)-3-cyclopentylphenyl]prop-2-en-1-ol crystallizes from petroleum ether, melting point: 78°–80° C.

¹H-NMR (60 MHz, CDCl₃, δ in ppm):
1.2–2.2 (m, 8–9H), 3.03 (t, 6–7Hz, 2H), 3.2–3.7 (m, 1H), 3.93 (t, 6–7Hz, 2H), 4.13 (d, 5.5–6Hz, 2H), 6.0–6.4 (m, 1H), 7.27 (s), 6.7–7.4 (m) Σ 8H (2RS,3RS)3-[2 -(2-Phenylethoxy)-3-cyclopentylphenyl]-2,3-epoxypropanol Methyl (5RS),(6SR)-5-[2-(2-phenylethoxy)-3-cyclopentylphenyl]-6,7-dihydroxy-4-thiaheptanoate ¹H-NMR (270 MHz, CDCl₃, δ in ppm):
1.4–1.1.68 (m, 4H), 1.77 (m, 2H), 1.93 (m, 2H), 2.31 (s br, 2H), 2.500 (m, 2H), 2.618 (m, 2H), 3.104 (t, 6Hz)+3.0–3.15 (m) Σ 3H, 3.5–3.7 (m)+3.666 (s) Σ 5H, 3.9–4.1 (m, 3H), 2.240 (d, 7Hz, 1H), 7.092 (t, 8Hz, 1H), 7.170 (dd, 8Hz, 1–2Hz, 1H), 7.263 (dd, 8Hz, 1–2Hz, 1H), 7.326 (m, 5H)

Methyl (5RS),(6SR)-5-[2-(2-phenylethoxy)-3-cyclopentylphenyl]-6-hydroxy-7-(4-methanesulfonyloxy)-4-thiaheptanoate ¹H-NMR (60 MHz, CDCl₃, δ in ppm):
1.2–2.2 (m, 8–9H), 2.55 (t, 7Hz, 2H), 2.6–3.3 (m)+3.00 (s)+3.10 (t, 6–7Hz) Σ 7–8H, 3.3–3.8 (m)+3.70 (s) Σ 4H, 3.8–4.3 (m, 5H), 7.0–7.5 (m, 8H)

EXAMPLE 40

Dimethyl (5RS),(6SR)-6-(2-pentyloxy-3-cyclopentylphenyl)-5-hydroxy-3,7-dithiadecanedioate ¹H-NMR (270 MHz, CDCl₃, δ in ppm): 0.96 (t, 7Hz, 3H), 1.35–1.6 (m, 6H), 1.6–1.75 (m, 2H), 1.75–1.9 (m, 4H), 1.95–2.1 (m, 2H), 2.55 (m, 2H), 2.68 (m, 2H), 2.78 (dd, 15Hz, 8Hz, 1H), 3.055 (dd, 15Hz, 3–4Hz, 1H), 3.32 (m, 1H), 3.35 (s, 2H), 3.66 (s, 3H), 3.71 (s, 3H), 3.75–3.95 (m, 2H), 4.14 (m, 1H), 4.49 (d, 8Hz, 1H), 7.10 (t, 8Hz, 1H), 7.19 (dd, 8Hz, 2Hz, 1H), 7.31 (dd, 8Hz, 2Hz, 1H) is obtained in analogy to Example 37 via the following intermediates:

2-Pentyloxy-3-cyclopentylbenzaldehyde (from Example 37, stage 1 and n-pentyl bromide)

¹H-NMR (60 MHz, CDCl₃, δ in ppm): 0.93 (t br, 3H), 1.2–2.2 (m, 14H), 3.0–3.6 (m, 1H), 3.88 (t, 6Hz, 2H), 6.6–7.8 (m, 3H), 10.33 (s, 1H)

(E)-3-(2-Pentyloxy-3-cyclopentylphenyl)propenoic acid

¹H-NMR (60 MHz, CDCl₃, δ in ppm): 0.96 (m, 3H), 1.1–2.3 (m, 14 H), 3.0–3.6 (m, 1H), 3.80 (t, 6Hz, 2H), 6.46 (d, 16Hz, 1H), 6.9–7.6 (m,3H), 8.17 (d, 16Hz, 1H)

Methyl (E)-3-(2-pentyloxy-3-cyclopentylphenyl)-propenoate

¹H-NMR (60 MHz, CDCl₃, δ in ppm):
0.95 (m, 3H), 1.1–2.3 (m, 14H), 3.0–3.6 (m, 1H), 3.80 (t, 6Hz), 3.83 (s) Σ 5H, 6.45 (d, 16Hz, 1H), 6.9–7.6 (m,3H), 8.03 (d, 16Hz, 1H)

(E)-3-(2-Pentyloxy-3-cyclopentylphenyl)prop-2-en-1-ol

¹H-NMR (60 MHz, CDCl₃, δ in ppm): 0.93 (t br, 3H), 1.0–2.3 (m,14H), 3.0–3.6 (m, 1H), 3.70 (t, 6Hz, 2H), 4.28 (d, 5.5–6Hz, 2H), 6.23 (dt, 16Hz, 5.5–6Hz, 1H), 6.6–7.5 (m, 4H) (2RS,3RS)-3-(2-Pentyloxy-3-cyclopentylophenyl)-2,3-epoxypropanol ¹H-NMR (60 MHz, CDCl₃, δ in ppm):
0.92 (t br, 3H), 1.0–2.3 (m,14H), 3.0–4.0 (m), 3.73 (t, 7Hz) Σ 6–7H), 4.11 (d, 2Hz, 1H), 6.8.–7.3 (m, 3H)

Methyl (5RS),(6SR)-5-(2-Pentyloxy-3-cyclopentylphenyl)-6,7-dihydroxy-4-thiaheptanopate ¹H-NMR (270 MHz, CDCl₃, δ in ppm):
0.959 (t, 7Hz, 3H), 1.35–1.6 (m), 1.65–1.9 (m) Σ 12H, 1.95–2.1 (m, 2H), 2.358 (d br, 4–5Hz, 1H), 2.437 (t br, 6Hz, 1H), 2.53–2.62 (m, 2H), 2.65–2.8 (m, 2H), 3.314 (quintuplet, 8–9Hz, 1H), 3.669 (s), 3.58–3.7 (m) Σ 5H, 3.7–3.9 (m, 2H), 4.047 (m, 1H), 4.488 (d, 7Hz, 1H), 7.115 (t, 8Hz, 1H), 7.205 (dd, 8Hz, 1–2Hz, 1H), 7.303 (dd, 8Hz, 1–2Hz, 1H)

Methyl (5RS),(6SR)-5-(2-pentyloxy-3-cyclopentylphenyl)-6-hydroxy-7-(4-methanesulfonyloxy)-4-thiaheptanoate 1.2 mmol (0.5 g) of methyl (5RS),(6SR)-5-(2-pentyloxy-3-cyclopentylphenyl)-6,7-dihydroxy-4-thiaheptanoate are dissolved in 5 ml of dry CH₂Cl₂. 0.27 ml of dry triethylamine is added, and the mixture is cooled under a nitrogen atomosphere to −10° to −20° C. 1.3 mmol of methanesulfonyl chloride dissolved in a little CH₂Cl₂ are added dropwise at this temperature, and the mixture is then left to stir for a further 30 min. and then allowed to reach room temperature. It is washed with 2N hydrochloric acid and water and dried over $Na_2SO_4$, and the solvent is removed by distillation in vacuo. The resulting product is used without further purification in the next stage.

$^1$H-NMR (60 MHz, CDCl$_3$, δ in ppm): 0.95 (m, 3H), 1.2–2.2 (m, 14H), 2.4–2.9 (m, 4–5H), 3.03 (s, 3H), 3.1–4.0 (m, 3–4H), 3.68 (s, 3H), 4.1–4.7 (m, 2H), 7.0–7.5 (m. 3H)

EXAMPLE 41

Dimethyl (5RS),(6SR)-6-(2-decyloxy-3-cyclopentylphenyl)-5-hydroxy-3,7-dithiadecanedioate $^1$H-NMR (270 MHz, CDCl$_3$, δ in ppm): 0.90 (t, 7Hz, 3H), 1.2–1.9 (4 m), 2.0–2.1 (m), 2.5–2.8 (m, ca. 4H), 3.06 (d br, 14Hz, 1H), 3.32 (quintuplet br, 7–8Hz, 1H), 3.35 (s, 2H), 3.65 (s, 3H), 3.73 (s, 3H), 3.75–3.9 (m, 2H), 4.14 (td, 8Hz, 3Hz, 1H), 4.49(d, 8Hz, 1H), 7.09 (t, 8Hz, 1H), 7.19 (dd, 8Hz, 3Hz, 1H), 7.32 (dd, 8Hz, 3Hz, 1H) is obtained in analogy to Example 37 via the following intermediates:

2-Decyloxy-3-cyclopentylbenzaldehyde (from Example 37, stage 1, and n-decyl bromide)

$^1$H-NMR (60 MHz), CDCl$_3$, δ in ppm):
0.86 (t br, 3H), 1.1–2.2 (m, 24H), 3.0–3.6 (m, 1H), 3.86 (t, 6Hz, 2H), 6.8–7.7 (m, 3H), 10.3 (s, 1H)

Ethyl (E)-3-(2-decyloxy-3-cyclopentylphenyl)propenoate (prepared in analogy to Example 38)

$^1$H-NMR (60 MHz, CDCl$_3$, δ in ppm):
0.88 (t br, 3H), 1.33 (t, 7Hz), 1.0–2.3 (m) Σ 27H, 3.0–3.6 (m, 1H), 3.80 (t, 6Hz, 2H), 4.28 (q, 7Hz, 2H), 6.44 (d, 16Hz, 1H), 6.9.–7.6 (m, 3H), 8.03 (d, 16Hz, 1H)

(E)-3-(2-Decyloxy-3-cyclopentylphenyl)prop-2-en-1-ol $^1$H-NMR (60 MHz, CDCl$_3$, δ in ppm): 0.86 (t br, 3H), 1.0–2.3 (m,24H), 3.0–3.6 (m, 1H), 3.70 (t, 6Hz, 2H), 4.27 (d, 5.5–6Hz, 2H), 6.23 (dt, 16Hz, 5.5–6Hz, 1H), 6.6–7.5 (m, 4H)

(2RS,3RS),-3-(2-Decyloxy-3-cyclopentylphenyl)-2,3-epoxypropanol

Methyl (5RS),(6SR)-5-(2-decyloxy-3-cyclopentylphenyl)-6,7-dihydroxy-4-thiaheptanoate $^1$H-NMR (270 MHz, CDCl$_3$, δ in ppm): 0.89 (t, 7Hz, 3H), 1.2–1.9 (m, 22H), 1.95–2.1 (m, 2H), 2.36 (s br, 1H), 2.44 (s, br, 1H), 2.54–2.61 (m, 2H), 2.70–2.77 (m, 2H), 3.31 (quintuplet, 8–9Hz, 1H), 3.667 (s, 3H), 3.4–3.7 (m, 2H), 3.75–3.91 (m, 2H), 4.0–4.1 (m, 1H), 4.487 (d, 8Hz, 1H), 7.111 (t, 8Hz, 1H), 7.206 (dd, 8Hz, 3Hz, 1H), 7.304 (dd, 8Hz, 3Hz, 1H)

Methyl (5RS),(6SR)-5-(2-decyloxy-3-cyclopentylphenyl)-6-hydroxy-7-(4-methanesuylfonyloxy)-4-thiaheptanoate

EXAMPLE 42

Dimethyl (5RS),(6SR)-6-(2-dodecyloxy-3-cyclopentylphenyl)-5-hydroxy-3,7-dithiadecanedioate $^1$H-NMR (270 MHz, CDCl$_3$, δ in ppm): 0.89 (t, 7Hz, 3H), 1.2–1.9 (3 m), 2.2–2.1 (m), 2.5–2.8 (m, ca. 4H), 3.233, 3.22 (AB, 16 Hz, 2H), 3.30 (quintuplet br, 7–8Hz, 1H), 3.67 (s, 3H), 3.70 (s, 3H), 3.70 (s, 3H), 3.82 (t, 7Hz, 2H), 3.4–3.9 (m, 2H), 4.04 (quintuplet, 6Hz, 1H), 4.488(d, 7Hz, 1H), 7.11 (t, 8Hz, 1H), 7.204 (dd, 8Hz, 3Hz, 1H), 7.306 (dd, 8Hz, 3Hz, 1H) is obtained in analogy to Example 37 via the following intermediates:

2-Docecyloxy-3-cyclopentylbenzaldehyde (from Example 37, stage 1 and n-dodecyl bromide)

$^1$H-NMR (60 MHz, CDCl$_3$, δ in ppm): 0.86 (t br, 3H), 1.1–2.2 (m, 28H), 3.0–3.6 (m, 1H), 3.91 (t, 6Hz, 2H), 6.8–7.7 (m, 3H), 10.4 (s, 1H)

(E)-3-(2-Dodecyloxy-3-cyclopentylphenyl)propenoic acid $^1$H-NMR (60 MHz, CDCl$_3$, δ in ppm): 0.86 (m, 3H), 1.1–2.3 (m, 28H), 3.0–3.6 (m, 1H), 3.76 (t, 6Hz, 2H), 6.43 (d, 16Hz, 1H), 6.9–7.6 (m, 3H), 8.12 (d, 16Hz, 1H)

Methyl (E)-3-(2-dodecyloxy-3-cyclopentylphenyl)-propenoate $^1$H-NMR (60 MHz, CDCl$_3$, δ in ppm): 0.86 (m, 3H), 1.1–2.3 (m, 28H), 3.0–3.6 (m, 1H), 3.76 (t, 6Hz),3.82 (s) Σ 5H, 6.43 (d, 16Hz, 1H), 6.9–7.6 (m,3H), 8.04 (d, 16Hz, 1H)

(E)-3- (2-Dodecyloxy-3-cyclopentylphenyl)prop-2-en-1-ol $^1$H-NMR (60 MHz, CDCl$_3$, δ in ppm):
0.86 (t br, 3H), 1.0–2.3 (m,28H), 3.0–3.6 (m, 1H), 3.75 (t, 6Hz, 2H), 4.33 (d, 5.5–6Hz, 2H), 6.0–6.6 (m, 1H), 6.6–7.5 (m, 4H)

(2RS,3RS)-3-(2-Dodecyloxy-3-cyclopentylphenyl)-2,3-epoxy-propanol $^1$H-NMR (60 MHz, CDCl$_3$, δ in ppm):
0.87 (t br, 3H), 1.0–2.3 (m,28H), 3.0–4.0 (m), 3.72 (t) Σ 6–7H, 4.22 (m, 1H), 6.8–7.4 (m, 3H)

Methyl (5RS), (6SR)-5-(2-dodecyloxy-3-cyclopentylphenyl)-6,7-dihydroxy-4-thiaheptanoate $^1$H-NMR (270 MHz, CDCl$_3$, δ in ppm): 0.89 (t, 7Hz, 3H), 1.25–1.9, 2.0–2.1 (m), 2.364 (d, 5Hz, 1H), 2.457 (t, 7HZ, 1H), 2.54–2.60 (m, 2H), 2.7–2.8 (m, 2H), 3.316 (m, 1H), 3.670 (s, 3H), 3.6–3.75 (m, 2H), 3.75–3.9 (m, 2H), 4.054 (m, 1H), 4.486 (d, 8Hz, 1H), 7.113 (t, 8Hz, 1H), 7.204 (dd, 8Hz, 3Hz, 1H), 7.309 (dd, 8Hz, 3Hz, 1H)

Methyl (5RS),(6SR)-5-(2-dodecyloxy-3-cyclopentylphenyl)-6-hydroxy-7-(4-methanesulfonyloxy)-4-thiaheptanoate

EXAMPLE 43

Dimethyl (5RS),(6SR)-6-(2-undecyloxy-3-cyclopentylphenyl)-5-hydroxy-3,7-dithiadecanedioate $^1$H-NMR (270 MHz, CDCl$_3$, δ in ppm): 0.89 (t, 7Hz, 3H), 1.2–1.4 (m), 1.4–1.6 (m), 1.6–1.9 (m), 2.0–2.1 (m), 2.5–2.8 (m, ca. 4H), 3.235, 3.26 (AB, 16.4 Hz, 2H), 3.31 (quintuplett br, 7–8Hz, 1H), 3.67 (s, 3H), 3.70 (s, 3H), 3.82 (t, 7Hz, 2H), 3.4–3.9 (m, 2H), 4.04 (quintuplett, 6Hz, 1H), 4.488(d, 7Hz, 1H) is obtained in analogy to Example 37 via the following intermediates:

2-Undecyloxy-3-cyclopentylbenzaldehyde (from Example 37, stage 1 and n-undecyl bromide)

$^1$H-NMR (60 MHz, CDCl$_3$, δ in ppm): 0.86 (t br, 3H), 1.1–2.2 (m, 26H), 3.0–3.6 (m, 1H), 3.87 (t, 6Hz, 2H), 6.8–7.8 (m, 3H), 10.32 (s, 1H)

Ethyl (E)-3-(2-undecyloxy-3-cyclopentylphenyl)-propenoate $^1$H-NMR (60 MHz, CDCl$_3$, δ in ppm): 0.86 (t br, 3H), 1.33 (t, 7Hz), 1.0–2.3 (m) Σ 29H, 3.0–3.6 (m, 1H), 3.72 (t, 6Hz, 2H), 4.23 (q, 7Hz, 2H), 6.35 (d, 16Hz, 1H), 6.9.–7.6 (m, 3H), 7.93 (d, 16Hz, 1H)

(E)-3-(2-Undecyloxy-3-cyclopentylphenyl)prop-2-en-1-ol $^1$H-NMR (60 MHz, CDCl$_3$, δ in ppm): 0.86 (t br, 3H), 1.0–2.3 (m,26H), 3.0–3.6 (m, 1H), 3.77 (t, 6Hz, 2H), 4.35 (d, 5.5–6Hz, 2H), 6.0–6.6 (m, 1H), 6.6.–7.5 (m, 4H)

(2RS,3RS)-3-(2-Undecyloxy-3-cyclopentylphenyl)-2,3-epoxypropanol

Methyl (5RS), (6SR)-5-(2undecyloxy-3-cyclopentylphenyl)-6,7-dihydroxy-4-thiaheptanoate $^1$H-NMR (270 MHz, CDCl$_3$, δ in ppm):
0.89 (t, 7Hz, 3H), 1.25–1.45, 1.45–1.6, 1.65–1.75, 1.75–1.9, 2.0–2.1 (m, Σ 26H), 2.367 (d, 5Hz, 1H), 2.456 (t, 7HZ, 1H), 2.54–2.61 (m, 2H), 2.7–2.8 (m, 2H), 3.318 (m, 1H), 3.669 (s, 3H), 3.6–3.75 (m, 2H), 3.75–3.9 (m, 2H), 4.052 (m, 1H), 4.488 (d, 8Hz, 1H), 7.115 (t, 8Hz, 1H), 7.206 (dd, 8Hz, 3Hz, 1H), 7.311 (dd, 8Hz, 3H, 1H)

Methyl (5RS),(6SR)-5-(2-undecyloxy-3-cyclopentylphenyl)-6-hydroxy-7-(4-methanesulfonyloxy)-4-thiaheptanoate $^1$H-NMR (60 MHz, CDCl$_3$, δ in ppm): 0.85 (m, 3H), 1.1–2.2 (m, 26H), 2.5–2.8 (m, 4H), 3.0 (s, 3H), 3.63 (s, 3H), 3.75–3.9 (m, 1H), 4.2–4.5 (m, 3H), 7.0–7.4 (m, 3H)

EXAMPLE 44

Dimethyl (5RS),(6SR)-6-[2-(2-pyridylmethyloxy)-3-cyclopentylphenyl]-5-hydroxy-3,7-dithiadecanedioate $^1$H-NMR (270 MHz, CDCl$_3$, δ in ppm): 1.5–1.8 (m, 6H), 2.0–2.15 (m, 2H), 2.408 (t, 7Hz, 2H), 2.55–2.7 (m, 2H), 2.724 (dd, 15Hz, 8Hz, 1H), 3.018 (dd, 15Hz, 3–4Hz, 1H), 3.321 (s, 2H), 3.45–3.5 (m, 1H), 3.612 (s, 3H), 3.691 (s, 3H), 4.0–4.1 (m, 1H), 4.73 (d, 8Hz, 1H), 4.905, 5.155 (AB, 12Hz, 2H), 7.173 (t, 7Hz, 1H), 7.232 (dd, 7Hz, 1–2Hz, 1H), 7.314 (dd, 5–6Hz, 7–8Hz, 1H), 7.390 (dd, 7Hz, 1–2Hz, 1H), 7.552 (d, 8Hz, 1H), 7.81 (td, 8Hz, 1–2Hz, 1H), 8.639 (d br, 5–6Hz, 1H) is obtained in analogy to Example 37 via the following intermediates:

2-(2-Pyridylmethyloxy)-3-cyclopentylbenzaldehyde (from Example 37, stage 1and 2-bromomethylpyridine)

$^1$H-NMR (60 MHz, CDCl$_3$, δ in ppm): 1.5–2.2 (m, 8H), 3.0–3.6 (m, 1H), 5.07 (s, 2H), 7.0–7.9 (m, 6H), 8.57 (d br, 4–5Hz, 1H), 10.30 (s, 1H)

Ethyl (E)-3-[2-(2-pyridylmethyloxy)-3-cyclopentylphenyl]-propenoate $^1$H-NMR (60 MHz, CDCl$_3$, δ in ppm):
1.23 (t, 7Hz), 1.5–2.2 (m, 8H), 3.0–3.6 (m, 1H), 4.15 (q, 7Hz, 2H), 4.90 (s, 2H), 6.35 (d, 16Hz, 1H), 6.9–7.9 (m, 6H), 7.87 (d, 16Hz, 1H), 8.53 (d br, 4–5Hz, 1H)

(E)-35-[2-(2-Pyridylmethyloxy)-3-cyclopentylphenyl]-prop-2-en-1-ol $^1$H-NMR (60 MHz, CDCl$_3$, δ in ppm):
1.4–2.2 (m, 8H) 3.0–3.6 (m, 1H), 4.19 (d br, 5.5–6Hz, 2H), 4.87 (s, 2H), 6.26 (dt, 16Hz, 5.5–6Hz, 1H), 6.6–7.8 (m, 7H), 8.49 (d br, 5Hz, 1H)

(2RS,3RS)-3-[2-(2-Pyridylmethyloxy)-3-cyclopentylphenyl]-2,3-epoxypropanol $^1$H-NMR (60 MHz, CDCl$_3$, δ in ppm): 1.4–2.2 (m, 8H), 3.0–3.6 (m, 1H), 3.8–4.4 (m, 4H), 4.91 (s br, 2H), 7.0–8.0 (m, 6H), 8.58 (d br, 4–5Hz, 1H)

Methyl (5RS),(6SR)-5-[2-(2-pyridylmethyloxy)-3-cyclopentylphenyl]-6,7-dihydorxy-4-thiaheptanoate $^1$-H NMR (270 MHz, CDCl$_3$, δ in ppm): 1.5–1.8 (m, 6H), 2.0–2.15 (m, 2H), 2.43 (t, 7Hz, 2H), 2.55–2.70 (m, 2H), 3.41 (quintuplet, 7–9Hz), 3.3–3.45 (s br) Σ 3H, 3.607 (s, 3H), 3.76 (d, 6Hz, 2H), 4.03 (m, 1H), 4.74 (d, 8Hz, 1H), 4.903, 5.170 (AB, 12Hz, 2H), 7.177 (t, 7Hz, 1H), 7.229 (dd, 7Hz, 1–2Hz, 1H), 7.318 (dd, 5–6Hz, 7–8 Hz, 1H), 7.394 (dd, 7Hz, 1–2Hz, 1H), 7.548 (d, 8Hz, 1H), 7.802 (td, 8Hz, 1–2Hz, 1H), 8.641 (d br, 5–6Hz, 1H)

Methyl (5RS),(6SR)-5-[2-(2-pyridylmethyoxy)-3-cyclopentylphenyl]-6-hydroxy-7-(4-methanesulfonyloxy)-4-thiaheptanoate $^1$H-NMR (60 MHz), CDCl$_3$, δ in ppm):
1.2–2.1 (m, 8H), 2.1–2.8 (m, 4–5H), 2.43 (s, 3H), 3.61 (s, 3H), 3.0–4.8 (m, 3–4H), 5.01 (s, br, 2H), 7.0–7.5 (m, 7H), 7.70 (m, 1H), 7.80 (d, 8Hz, 2H), 8.70 (m, 1H)

EXAMPLE 45

Disodium (5RS),(6SR)-6-[2-benzyloxy-3-cyclopentylphenyl]-5-hydroxy-3,7-dithiadecanedioate 1 mmol of dimethyl (5RS),(6SR)-6-[2-benzyloxy-3-cyclopentylphenyl]-5-hydroxy-3,7-dithiadecanedioate (Example 37) is dissolved in 10 ml of methanol, and 1 ml of 2N NaOH in methanol is added. The mixture is stirred under a nitrogen atmosphere at room temperature for 16 h, the solution is evaporated in vacuo, and the residue is dried under oil pump vacuum at 50° C. A somewhat hygroscopic pale powder is obtained.
Melting point: 139°–140° C.

EXAMPLE 46

Dimethyl (5RS),(6SR)-5-[2-benzyloxy-3-cyclopentylphenyl]-6-hydroxy-4,8-dithiaundecanedioate prepared in analogy to Example 37 from methyl (5RS),(6SR)-5-(2-benzyloxy-3-cyclopentylphenyl)-6-hydroxy-7-(4-methanesulfonyloxy)-4-thiaheptanoate (Example 37, stage 8) and methyl 3-mercaptopropionate.

$^1$H-NMR (60 MHz, CDCl$_3$, δ in ppm): 1.2–2.2 (m, 8H), 2.3–2.9 (m, 10H), 3.65 (s, 3H), 3.69 (s, 3H), 3.8–4.3 (m, 1H), 4.50 (d, 7–8Hz, 1H), 4.87 4.99 (AB, 11.5Hz, 2H), 7.0–7.7 (m, 8H)

EXAMPLE 47

Dimethyl (5RS),(6SR)-5-[2-decyloxy-3-cyclopentylphenyl]-6-hydroxy-4,8-dithiaundecanedioate prepared in analogy to Example 37 from methyl (5RS),(6SR)-5-(2-decyloxy-3-cyclopentylphenyl)-6hydroxy-7-(4-methanesulfonyloxy)-4-thiaheptanoate (see Example 41) and methyl 3-mercaptopropionate.

$^1$H-NMR (270 MHz, CDCl$_3$, δ in ppm): 0.89 (t, 7Hz, 3H), 1.2–1.4 (m), 1.4–1.6 (m), 1.6–1.9 (m), 1.95–2.1 (m), 2.5–2.75 (m, 7H), 2.86 (t, 8Hz, 2H), 2.96 (dd, 14HZ, 4Hz, 1H), 3.32 (quintuplet br, 7–8Hz, 1H), 3.65 (s, 3H), 3.69 (s, 3H), 3.7–3.9 (m, 2H), 4.05–4.15 (m, 1H), 4.48 (d, 7Hz, 1H), 7.09 (t, 8Hz, 1H), 7.19 (dd, 8Hz, 1–2Hz), 7.32 (dd, 8Hz, 1–2Hz, 1H)

EXAMPLES 48

Dimethyl (5RS),(6SR)-5-[2-undecyloxy-3-cyclopentylphenyl]6-hydroxy-4,8-dithiaundecanedioate prepared in analogy to Example 37 from methyl (5RS),(6SR)-5-(2-undecyloxy-3-cyclopentylphenyl)-6-hydroxy-7-(4-methanesulfonyloxy)-4-thiaheptanoate (see Example 43) and methyl 3-mercaptopropionate.

$^1$H-NMR (270 MHz, CDCl$_3$, δ in ppm):
0.89 (t, 7Hz, 3H), 1.2–1.4 (m), 1.4–1.6 (m), 1.6–1.9 (m), 1.95–2.1 (m), 2.5–2.75 (m, 7H), 2.86 (t, 8Hz, 2H), 2.96 (dd, 14HZ, 4Hz, 1H), 3.31 (quintuplet br, 7–8Hz, 1H), 3.66 (s, 3H), 3.69 (s, 3H), 3.7–3.9 (m, 2H), 4.05–4.15 (m, 1H), 4.47 (d, 7Hz, 1H), 7.09 (t, 8Hz, 1H), 7.19 (dd, 8Hz, 1–2Hz), 7.32 (dd, 8Hz, 1–2Hz, 1H)

EXAMPLE 49

Methyl (5RS),(6SR)-6-(3-methoxyphenylthio)-6-(2-undecycloxy-3-cyclopentylphenyl)-5-hydroxy-3-thiahexanoate ¹H-NMR (270 MHz, CDCl₃, δ in ppm): 0.89 (t, 7Hz, 3H), 1.2–1.4 (m), 1.4–1.6 (m), 1.6–1.9 (m), 1.95–2.1 (m), 2.67 (dd, 14Hz, 8Hz, 1H), 2.98(dd, 14Hz, 4Hz, 1H), 3.28 (s, 2H), 3.3 (quintuplet br, 7–8Hz, 1H), 3.68 (s, 3H), 3.74 (s, 3H), 3.6–3.9 (m, 2H), 4.1–4.2 (m, 1H), 4.83 (d, 7Hz, 1H), 6.76 (ddd, 8Hz, 1–2Hz, 1 H), 6.92 ("t", 1–2Hz, 1H), 7.00 (dm, 8Hz, 1–2Hz, 1H), 7.0 (t, 8Hz, 1H), 7.16 (t, 8Hz, 1H), 7.19 (dd, 8Hz, 2–3Hz, 1H), 7.35 (dd, 8Hz, 1–2Hz) is obtained in analogy to Example 37 from (2RS,3RS)-3-(2-undecyloxy-3-cyclopentylphenyl)-2,3-epoxypropanol (see Example 43) via the following intermediates:

(2RS),(3SR)-3-(3-Methoxyphenylthio)-3-(2undecyloxy-3-cyclopentylphenyl)propane-1,2-diol ¹H-NMR (270 MHz, CDCl₃, δ in ppm):
0.89 (t, 7Hz, 3H), 1.2–1.4 (m), 1.45–1.6 (m), 1.6–1.9 (m), 2.0–2.1 (m)), 2.34 (s br, 1H), 2.41 (s br, 1H), 330 (quintuplet, 8Hz, 1H), 3.5–3.65 (m, 3H), 3.72 (s, 3H), 3.7–3.8 (m, 1H), 4.05–4.15 (m, 1H), 4.83 (d, 8Hz, 1H), 6.77 (ddd, 8Hz, 2–3Hz, 1–2Hz, 1H), 6.95 ("t", 1–2Hz, 1H), 7.02 (dm, 8Hz, 1–2Hz, 1H), 7.10 (t, 8Hz, 1H), 7.18 (t, 8Hz, 1H), 7.21 (dd, 8Hz, 2–3Hz, 1H), 7.34 (dd, 8Hz, 1–2Hz)

(2RS),(3SR)-1-Methanesulfonyloxy-3-(3-methoxyphenylthio)-3-(2-undecyloxy-3-cyclopentylphenyl)-propan-2-ol ¹H-NMR (60 MHz, CDCl₃, δ in ppm): 2.90 (s, 3H), 3.70 (s, 3H).

EXAMPLE 50

Dimethyl (5RS),(6SR)-6-(2-benxyloxyphenyl)-5-hydroxy-3,7-dithiadecanedioate

¹H-NMR (60 MHz, CDCl₃, δ in ppm): 2.4–3.0 (m, 7H), 3.23 (s, 2H), 3.60 (s, 3H), 3.64 (s, 3H), 3.9–4.15 (m, 1H), 4.56 (d, 6Hz, 1H), 5.0 (s, 2H), 6.8–7.6 (m, 9H) is obtained in analogy to Example 37 starting from 2-benzyloxybenzaldehyde via the following intermediates:

Ethyl (E)-3-(2-benzyloxyphenyl)acrylate

¹H-NMR (60 MHz, CDCl₃, δ in ppm):
1.32 (t, 7Hz, 3H), 4.27 (q, 7Hz, 2H), 5.19 (s, 2H), 6.54 (d, 17Hz, 1H), 6.8–7.7 (m, 9H), 8.12 (d, 17Hz, 1H)

(E)-3-(2-Benzyloxyphenyl)allyl alcohol

¹H-NMR (60 MHz, CDCl₃, δ in ppm):
1.54 (s br, 1H), 4.21 (d br, 5.5Hz, 2H), 5.04 (s, 2H), 6.26 (dt, 15Hz, 5.5Hz, 1H), 6.7–7.6 (m, 10H)

3-(2-Benzyloxyphenyl)-2,3-epoxyl-1-propanol

Methyl 5-(2-benzyloxyphenyl)-6,7-dihydroxy-4-thiaheptanoate

¹H-NMR (60 MHz, CDCl₃, δ in ppm):
2.33 (s, 2H), 2.4–2.8 (m, 4–5H), 3.65 (s+m, 5H), 3.9–4.1 (m, 1H), 4.54 (d, 6Hz, 1H), 5.07 (s, 2H), 6.8–7.6 (m, 9H)

Methyl 5-(2-benzyloxyphenyl)-6-hydroxy-7-methanesulfonyloxy-4-thiaheptanoate

¹H-NMR (60 MHz, CDCl₃, δ in ppm):
2.4–2.8 (m, 4–5H), 2.88 (s, 3H), 3.58 (s, 3H), 4.2–4.6 (m, 4H), 5.03 (s, 2H), 6.8–7.6 (m, 9H)

EXAMPLE 51

Disodium (5RS),(6SR)-6[2-benzyloxyphenyl]-5-hydroxy-3,7-dithiadecanedioate is obtained by hydrolysis of Example 50 in analogy to Example 45. Somewhat hygroscopic white solid.
Melting point >200° C. (decomposition)

EXAMPLE 52

Dimethyl (5RS),(6SR)-6-(2-methoxyphenyl)-5-hydroxy-3,7-dithiadecanedioate
¹H-NMR (60 MHz, CDCl₃, δ in ppm): 2.4–3.0 (m, 7H), 3.27 (s, 2H), 3.63 (s, 3H), 3.68 (s, 3H), 3.82 (s, 3H), 3.95–4.15 (m, 1H), 4.50 (d, 5.5Hz, 1H), 6.7–7.6 (m, 4H) is obtained in analogy to Example 37 starting from 2-methoxybenzaldehyde via the following intermediates:

Ethyl (E)-3-(2-methoxyphenyl)acrylate
¹H-NMR (60 MHz, CDCl₃, δ in ppm):
1.33 (t, 7Hz, 3H), 3.88 (s, 3H), 4.23 (q, 7Hz, 2H), 6.47 (d, 16Hz, 1H), 6.8–7.6 (m, 4H), 7.93 (d, 16Hz, 1H)

(E)-3-2-Methoxyphenyl)allyl alcohol
¹H-NMR (60 MHz, CDCl₃, δ in ppm):
1.91 (s br, 1H), 3.81 (s, 3H), 4.27 (dd, 6Hz, 1–2Hz, 2H), 6.26 (dt, 16Hz, 6Hz, 1H), 6.7–7.5 (m, 5H)

3-(2-Methoxyphenyl)-2,3-epoxy-1-propanol

Methyl 5-(2-methoxyphenyl)-6,7-dihydroxy-4-thiaheptanoate
¹H-NMR (60 MHz, CDCl₃, δ in ppm):
2.48 (s, 2H), 2.4–2.8 (m, 4H), 3.63 (s+m, 5H), 3.83 (s, 3H), 3.8–4.2 (m, 1H), 4.48 (d, 6Hz, 1H), 6.7–7.6 (m, 4H)

Methyl 5-(2-methoxyphenyl)-6-hydroxy-7-methanesulfonyloxy-4-thiaheptanoate
¹H-NMR (60 MHz, CDCl₃, δ in ppm):
2.4–3.0 (m, 5H), 2.97 (s, 3H), 3.60 (s, 3H), 3.79 (s, 3H), 4.2–4.6 (m, 4H), 6.7–7.6 (m, 4H)

EXAMPLE 53

Disodium (5RS),(6SR)-6-(2-methoxyphenyl-5-hydroxy-3,7-dithiadecanedioate is obtained by hydrolysis of Example 52 in analogy to Example 45. Somewhat hygroscopic white solid.
Melting point >200° C. (decomposition)

EXAMPLE 54

Methyl (5RS),(6SR)-6-(2-methoxyphenyl)-6-(3-methoxyphenylthio)-5-hydroxy-3-thiahexanoate
¹H-NMR (60 MHz, CDCl₃, δ in ppm): 2.5–3–0 (m, 2H), 3.28 (s, 2H), 3.70 (s, 3H), 3.75 (s, 3H), 3.85 (s, 3H), 4.0–4.4 (m, 1H), 4.95 (d, 6Hz,m 1H), 6.6–7.6 (m, 8H) is prepared in analogy to Example 37 from 3-(2-methoxyphenyl)-2,3-epoxyl-1-propanol (see Example 52) via the following intermediates:

3-(2-Methoxyphenyl)-3-(3-methoxyphenylthio)-1-methanesulfonyloxy-2-propanol 3-(2-Methoxyphenyl)-3-(3-methoxyphenylthio)propane-1,2-diol
¹H-NMR (60 MHz, CDCl₃, δ in ppm): 2.41 (s, 2H), 3.68 (s)+3.4–3.7(m) Σ 5H), 3.81 (s, 3H), 3.9–4.3 (m, 1H), 4.83 (d, 6Hz,m 1H), 6.6–7.6 (m, 8H)

EXAMPLE 55

Sodium (5RS),(6SR)-6-(2-methoxyphenyl)-6-(3-methoxyphenylthio)-5-hydroxy-3-thiahexanoate is obtained by hydrolysis of Example 54 in analogy to Example 45. Somewhat hygroscopic white solid.
Melting point 184°–88° C. (decomposition)

EXAMPLE 56

Dimethyl (5RS),(6SR)-6-[2-benzyloxyphenyl]-5-acetoxy-4,8-dithiadecanedioate
1 mmol of dimethyl (5RS),(6SR)-6-[2-benzyloxyphenyl]-5-hydroxy-4,8-dithiadecanedioate (Example 50) is dissolved in 5 ml of dry pyridine. 0.5 ml of acetic anydride is added while cooling in an ice bath, and the mixture is then stirred in the ice bath for a further 30 min and subsequently at RT for 1 h (exclusion of moisture). The mixture is poured into 50 ml of ice-cold dilute ammonia solution, and after extraction with methyl t.-butyl ether the extracts are washed with water, dilute sulfuric acid, NaHCO$_3$ solution and saturated NaCl solution and dried over Na$_2$SO$_4$, and the solvent is removed by distillation in vacuo. An oil is obtained.

$^1$H-NMR (60 MHz, CDCl$_3$, δ in ppm):
1.96 (s, 3H), 2.4-3.0 (m, 7H), 3.15-3.3 (AB, 2H), 3.66 (s, 3H), 3.70 (s, 3H), 5.3-5.7 (m, 1H), 4.87 (d, 6Hz, 1H), 5.14 (s, 2H), 6.8-7.6 (m, 9H)

EXAMPLE 57

(−)-(5S),(6R)-5-Hydroxy-6-(3-methoxyphenylthio)-6-phenyl-3-thiahexanoic acid 10 mmol of methyl (−)-(5S),(6R)-5-hydroxy-6-(3-methoxyphenylthio)-6-phenyl-3-thiahexanoate (Example 32) are dissolved in 20 ml of methanol, and 5 ml of 4N sodium hydroxide solution are added. The mixture is stirred under a nitrogen atmosphere at RT until starting material is no longer detectable in the TLC (solvent cyclohexane/ethyl acetate 2:1). The solution is acidified to about pH 3 with 2N hydrochloric acid; most of the methanol is removed by distillation in vacuo. The residue is taken up in ethyl acetate, and the solution is washed with saturated NaCl solution, dried over Na$_2$SO$_4$ and concentrated in vacuo. A colorless oil is obtained.

Rf=0.74 (ethyl acetate) [α]$^D$=−110° (c=2, MeOH)
$^1$H-NMR (270 MHz, CDCl$_3$, δ in ppm):
2.76 (dd, 15Hz, 8Hz, 1H), 2.94 (dd, 16Hz, 4Hz, 1H), 3.30, 3.33 (AB, 16Hz, 2H), 3.71 (s, 3H), 4.13-4.2 (m, 1H), 4.37 (d, 8Hz, 1H), 6.76 (ddd, 8HZ, 3-4Hz, 1-2Hz, 1H), 6.82 (t, 1-2Hz, 1H), 6.92 (dt, 8Hz, 1-2Hz, 1H), 7.14 (t, 8Hz), 7.25-7.4 (m, 5H)

EXAMPLE 58

(+)-(5R),(6S)-5-Hydoxy-6-(3-methoxyphenylthio)-6-phenyl-3-thiahexanoic acid prepared in analogy to Example 57 from methyl (+)-(5R), (6S)-5-hydroxy-6-(3-methoxyphenylthio)-6-phenyl-3-thiahexanoate (Example 31).

Rf=0.74 (ethyl acetate) [α]$^D$=+110° (c=2, MeOH)
$^1$H-NMR identical to Example 57.

We claim:
1. A compound of the formula I:

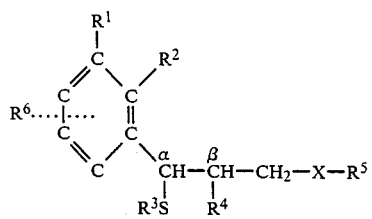

in which the radicals have the following meaning:
X is O, S, SO or SO$_2$;
R$^1$ is H, C$_1$-C$_{12}$-alkyl, C$_3$-C$_{12}$-alkenyl or C$_3$-C$_{12}$-alkynyl, C$_3$-C$_8$-cycloalkyl or C$_3$-C$_8$-cycloalkenyl, phenyl, halogen, CF$_3$, NO$_2$, phenoxy, OH, OR$^7$, COOH, COOR$^7$, CHO or COR$^8$;
R$^2$ is H, C$_1$-C$_{12}$-alkyl, C$_3$-C$_{12}$-alkenyl or C$_3$-C$_{12}$-alkynyl, phenyl-C$_1$-C$_{10}$-alkyl or a group OZ wherein Z is H, C$_1$-C$_{12}$-alkyl, C$_3$C$_{12}$-alkenyl or C$_3$-C$_{12}$-alkynyl, C$_3$-C$_8$-cycloalkyl or C$_3$-C$_8$-cycloalkenyl, phenyl, phenyl-C$_1$-C$_{10}$-alkyl, phenyl-C$_3$-C$_{10}$-alkenyl, phenyl-C$_3$-C$_{10}$-alkynyl or phenoxy-C$_2$-C$_6$-alkyl, it also being possible for the phenyl rings to be substituted by 1-3 C$_1$-C$_4$-alkyl, C$_2$-C$_4$-alkenyl, C$_1$-C$_4$-alkoxy, C$_1$-C$_4$-alkanoyl, C$_1$-C$_4$-alkoxycarbonyl, hydroxyl or halogen radicals;
R$_3$ is phenyl or phenyl substituted with 1-3 amino, halogen, hydroxyl, C$_1$-C$_4$-alkoxy, C$_1$-C$_4$-alkyl or C$_1$-C$_4$-alkylthio radicals, or R$^3$ is naphthyl, (CH$_2$)$_m$CO$_2$H or (CH$_2$)$_m$CO$_2$-C$_1$-C$_4$-alkyl;
R$^4$ is OH, C$_1$-C$_4$-alkoxy or OCOR$^8$;
R$^5$ is a group of the formula (CH$_2$)$_n$COR$^9$;
R$^6$ is H, halogen, CF$_3$, OH, C$_1$-C$_4$-alkyl or C$_1$-C$_4$alkoxy;
R$^7$ is C$_1$-C$_4$-alkyl, allyl or benzyl;
R$^8$ is C$_1$-C$_4$-alkyl;
R$^9$ is OH, C$_1$-C$_7$-alkoxy, OCH$_2$Ph, NHOH, NH$_2$, NHR$^8$, NR$^8$$_2$ or 2-carboxyphenoxy;
m is 1, 2, 3 or 4; and
n is 0, 1, 2 or 3;
as well as pharmaceutically acceptable salts of those compounds of the formula I in which one of the radicals contains a carboxyl group.

2. A compound as claimed in claim 1, of the formula I in which the radicals have the following meaning:
X is O, S, SO or SO$_2$;
R$^1$ is H, C$_3$-C$_8$-cycloalkenyl;
R$^2$ is H, straight-chain C$_8$-C$_{12}$-alkyl or C$_3$-C$_{12}$-alkenyl, phenyl-C$_1$-C$_{10}$-alkyl, or a group OZ, wherein Z is C$_1$-C$_{12}$-alkyl, C$_3$-C$_8$-cycloalkyl, phenyl, phenyl-C$_1$-C$_{10}$-alkyl or phenoxy-C$_2$-C$_6$-alkyl, it also being possible for the phenyl rings to be substituted by one to three methoxycarbonyl, acetyl, hydroxyl, C$_1$-C$_4$-alkyl or methoxy groups;
R$^3$ is phenyl or phenyl substituted with one to three amino, halogen, hydroxyl, C$_1$-C$_4$-alkoxy, C$_1$-C$_4$-alkyl or C$_1$-C$_4$-alkylthio radicals, or R$^3$ is naphthyl, (CH$_2$)$_m$CO$_2$H or (CH$_2$)$_m$CO$_2$-C$_1$-C$_4$-alkyl;
R$^4$ is OH;
R$^5$ is a group of the formula (CH$_2$)$_n$COR$^9$;
R$^6$ is H, halogen, C$_1$-C$_4$-alkyl or C$_1$-C$_4$-alkoxy;
R$^8$ is C$_1$-C$_4$-alkyl;
R$^9$ is OH, C$_1$-C$_7$-alkoxy, NH$_2$ or NHOH;
m is 1, 2, 3 or 4; and
n is 1, 2 or 3.

3. A compound as claimed in claim 1, of the formula I is which the radicals have the following meaning:
X is O or S;
R$^1$ is H or cyclopentyl;
R$^2$ is H, straight-chain C$_8$-C$_{12}$-alkyl or C$_3$-C$_{12}$-alkenyl, phenyl-C$_6$-C$_{10}$alkyl, or a group OZ, wherein Z is C$_1$-C$_{12}$-alkyl or phenyl-C$_1$-C$_{10}$-alkyl, it also being possible for the phenyl rings to be substituted by methoxycarbonyl or methoxy;
R$^3$ is phenyl or phenyl substituted with an amino, hydroxyl, methoxy, methyl or methylthio radical, or R$^3$ is naphthyl, (CH$_2$)$_m$CO$_2$H or (CH$_2$)$_m$CO$_2$-C$_1$-C$_4$-alkyl;
R$_4$ is OH;
R$^5$ is a group of the formula (CH$_2$)$_n$COR$^9$;
R$^6$ is H, halogen, C$_1$-C$_4$-alkyl or C$_1$-C$_4$-alkoxy;
R$^9$ is OH, C$_1$-C$_7$-alkoxy, NH$_2$ or NHOH;
m is 1, 2, 3 or 4; and
n is 1, 2 or 3.

4. Methyl (5RS,6 SR)-5-hydroxy-6-(3-methoxyphenylthio)-6-phenyl-3-oxahexanoate.

5. Dimethyl (5RS,6SR)-5-hydroxy-6-phenyl-3-oxa-7-thianonanedioate.

6. Dimethyl (5RS,6SR)-5-hydroxy-6-phenyl-3-oxa-7-thiadecanedioate.

7. Methyl (5RS,6SR)-5-hydroxy-6(3-methoxyphenylthio)-6phenyl-3-thiahexanoate.

8. Methyl (5S,6R)-(−)-5-hydroxy-6-(3-methoxyphenylthio)-6-phenyl-3-thiahexanoate.

9. Methyl (5R,6S)-(+)-5-hydroxy-6-(3-methoxyphenylthio)-6-phenyl-3-thiahexanoate.

10. Dimethyl (5RS,6RS)-5-hydroxy-6-phenyl-3,7-dithiadecanedioate.

11. Methyl (5RS,6SR)-5-hydroxy-6-(3-methoxyphenylthio)-6-(2-benzyloxy-3-cyclopentylphenyl)-3-oxahexanoate.

12. Dimethyl (5RS,6SR)-5-hydroxy-6-(2-benzyloxy-3-cyclopentylphenyl)-3-oxa-7-thianonanedioate.

13. Dimethyl (5RS,6SR)-5-hydroxy-6-(2-benzyloxy-3-cyclopentylphenyl)-3-oxa-7-thiadecanedioate.

14. Methyl (5RS,6SR)-5-hydroxy-6-(3-methoxyphenylthio)-6-(2-benzyloxy-3-cyclopentylphenyl)-3-thiahexanoate.

15. Dimethyl (5RS,6RS)-5-hydroxy-6-(2-benzyloxy-3-cyclopentylphenyl)-3,7-dithiadecanedioate.

16. Dimethyl (5RS,6RS)-5-hydroxy-6-[2-(4-methoxybenzyloxy) 3-cyclopentylphenyl]-3,7-dithiadecanedioate.

17. Methyl (5RS,6SR)-5-hydroxy-6-(3-methoxyphenylthio)-6-[2-(4-methoxybenzyloxy)-3-cyclopentylphenyl]-3-thiahexanoate.

18. (5S,6R)-(−)-5-Hydroxy-6-(3-methoxyphenylthio)-6-phenyl-3-thiahexanoic acid.

19. A pharmaceutical composition comprising an amount effective for use in the therapy of a mammal of a compound of the formula I according to claim 1 or of a physiologically tolerated salt of a compound of the formula I in which one of the radicals contains a carboxyl group, together with a pharmaceutically acceptable carrier.

20. A method for the treatment of a mammal suffering from a disorder associated with elevated levels of leukotrienes which comprises administering to said mammal an amount effective for said treatment of a pharmaceutical composition according to claim 19.

21. The method of claim 20 for the treatment of a mammal suffering from asthma.

22. A method for the treatment of a mammal suffering from a disorder associated with elevated levels of leukotrienes which comprises administering to said mammal an amount effective for said treatment of a compound of the formula I according to claim 1 or of a physiologically tolerated salt of a compound of the formula I in which one of the radicals contains a carboxyl group.

23. The method of claim 22 for the treatment of a mammal suffering from asthma.

* * * * *